United States Patent

Kim et al.

Patent Number: 6,030,978
Date of Patent: Feb. 29, 2000

[54] ANTIFUNGAL FORMULATION COMPRISING PROTOBERBERINE DERIVATIVES AND SALTS THEREOF

[75] Inventors: Jung Ho Kim, Daejeon; Tae Neung Jhong, Kyonggi-do; Young Ki Paik, Seoul; Joon Seo Park; Eui Deok Kim, both of Daejeon; You Suk Lee; Seung Un Kim, both of Seoul, all of Rep. of Korea

[73] Assignee: Hanwha Corporation, Seoul, Rep. of Korea

[21] Appl. No.: 09/208,641

[22] Filed: Dec. 10, 1998

[30] Foreign Application Priority Data

Apr. 24, 1998 [KR]  Rep. of Korea ............... 98/14795

[51] Int. Cl.⁷ ................................................... A61K 31/44
[52] U.S. Cl. ............................................ 514/280; 514/284
[58] Field of Search ...................................... 514/280, 284

[56] References Cited

U.S. PATENT DOCUMENTS

| | | | |
|---|---|---|---|
| 4,749,708 | 6/1988 | Maroko | 514/284 |
| 4,761,417 | 8/1988 | Maroko | 514/284 |
| 4,980,344 | 12/1990 | Maroko | 514/26 |
| 5,153,178 | 10/1992 | Maroko | 514/26 |

FOREIGN PATENT DOCUMENTS

| | | |
|---|---|---|
| 2043218 | 3/1972 | Germany . |
| 0143914 | 11/1980 | Japan . |
| 1004077 | 9/1965 | United Kingdom . |
| 1265627 | 3/1972 | United Kingdom . |
| 9800013 | 1/1998 | WIPO . |

OTHER PUBLICATIONS

V.M. Mahajan, et al., "Antimycotic Activity of Berberine Sulphate: An Alkaloid From an Indian Medicinal Herb," Sabouraudia (1982), 20, 79–81.

Primary Examiner—Allen J. Robinson
Attorney, Agent, or Firm—Birch, Stewart, Kolasch & Birch, LLP

[57] ABSTRACT

The antifungal formulation comprising the novel compounds of the following chemical formulae (I) and (II) exhibit in vitro antifungal activity against fungi including cutaneous filamentous fungus, such as Epidermophyton, Microsporum, Trichophyton, *Sporothrix schenckii*, Aspergillus or Candida. The formulation of the present invention exhibit in vitro antifungal activity at the concentration of 1–100 μg/ml.

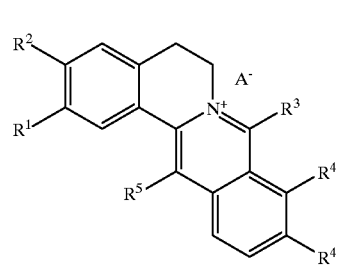

(I)

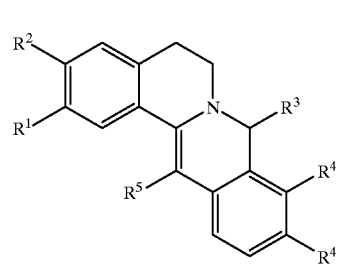

(II)

wherein $R^1$, $R^2$, and $R^4$ may be the same or different, and represent $C_1$–$C_5$ alkoxy, $R^3$ represents hydrogen or $C_1$–$C_{10}$ alkyl, $A^-$ represents inorganic acid ion, organic acid ion or halide, $R^5$ represents hydrogen, pyridylmethyl, substituted pyridylmethyl or a group having the following chemical formula(XI)

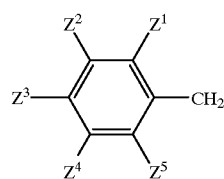

(XI)

wherein $Z^1$, $Z^2$, $Z^3$, $Z^4$ and $Z^5$ may be the same or different and represent hydrogen, halogen, $C_1$–$C_5$ alkyl, trifluoromethyl, phenyl, substituted phenyl, nitro, $C_1$–$C_4$ alkoxy, $C_1$–$C_4$ alkylamino, acetylamino, $C_1$–$C_8$ trialkyl ammonium, guanidinyl, methylthio, ethylthio, trifluoromethoxy, hydroxy, phenoxy, vinyl, carboxyl and $C_1$–$C_2$ alkoxycarbonyl group.

13 Claims, No Drawings

ANTIFUNGAL FORMULATION COMPRISING PROTOBERBERINE DERIVATIVES AND SALTS THEREOF

TECHNICAL FIELD

The present invention relates to an antifungal formulation comprising pharmaceutically available protoberberine derivatives and salts thereof More particularly, the present invention relates to an antifungal formulation comprising protoberberine salt derivatives, which have the following chemical formula (I) and the reduction product thereof, i.e., 7,8-dihydroprotoberberine derivative and salt thereof

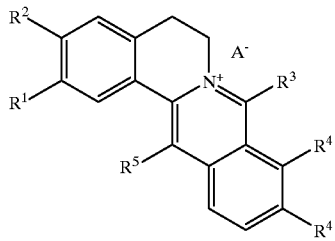

(I)

wherein $R^1$, $R^2$ and $R^4$ may be the same or different, and represent $C_1$–$C_5$ alkoxy, $R^3$ represents hydrogen or $C_1$–$C_{10}$ alkyl, $A^-$ represents inorganic acid ion, organic acid ion or halide, $R^5$ represents hydrogen, pyridylmethyl, substituted pyridylmethyl or a group having the following chemical formula (XI)

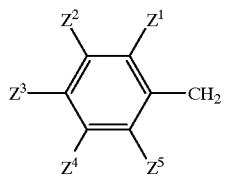

(XI)

wherein $Z^1$, $Z^2$, $Z^3$, $Z^4$ and $Z^5$ may be the same or different, and independently of one another represent hydrogen, halogen, $C_1$–$C_5$ alkyl, trifluoromethyl, phenyl, substituted phenyl, nitro, $C_1$–$C_4$ alkoxy, $C_1$–$C_4$ alkylamino, acetylamino, $C_1$–$C_8$ trialkyl ammonium, guanidinyl, methylthio, ethylthio, trifluoromethoxy, hydroxy, phenoxy, vinyl, carboxyl and $C_1$–$C_2$ alkoxycarbonyl groups.

BACKGROUND ART

Huanglian, Coptis spp., a traditional drug in the oriental region, is the root of barberry shrub and has been used as a drug for conjunctivitis, diarrhoea etc., from ancient times. The present invention provides novel compounds having antibiotic activities, which is related to berberine, i.e., alkaloid component of Huanglian, Coptis spp.

Berberine chloride exhibits antibacterial activity against Gram-negative or Gram-positive bacteria, such as *Staphylococcus aureus, Staphylococcus hemolyticus, Salmonella typhosa, Shigella dysenteriae, Shigella paradysenteriae, Escherichia coli Neisseria gonorrhoeae* or *Diplococcus pneumoniae* [Ukita T, Mizuno D, Tamura T, Jpn J Exp Med 20, 103 (1949)]. It has been reported that quaternary ammonium salt of berberine is prerequisite to the above antibacterial activity, and that the derivatives which do not contain such quaternary ammonium salt, for example, tetrahydroberberine exhibits less effect [Pitea. M, Margineanu C, *Clujul Med* 45, 465(1972)].

In addition, it has been reported that berberine sulfate inhibits the growth of fungi, such as Alternaria sp., *Aspergillus flavus, Aspergillus fumigatus, Candida albicans,* Curvularia sp., Drechslera sp., Fusarium sp., Mucor sp., Penicillium sp., *Rhizopus oryzae*, or Scopulariopsis sp. at 10–25 mg/ml [Mahajan V M, Sharma A, Rattan A, Sabouraudia 20, 79 (1982)], and that berberine sulfate is also effective in case of oral administration of 350–700 mg/kg for mice infected with *Candida albicans* [Mirska I, Kedzia H, Kowalewski Z, Kedzia W, *Arch Immunol. Ther Exp* 20, 921 (1972)].

However, the antifungal activities of the compounds disclosed in the above prior arts are too weak. Moreover, berberine sulfate exhibits intense toxicity and thereby may cause a harmful or lethal effect on human in case of being dosed excessively. Accordingly, the present invention is contrived to solve these disadvatages.

DISCLOSURE OF INVENTION

On the basis of the above mentioned prior art, the present inventors have prepared novel berberine analogous compounds from the berberine compound, and as a result, have found that these novel compounds exhibit fungicidal effect or growth-inhibitory effect against fungi including cutaneous filamentous fungus, such as Epidermophyton, Microsporum, Trichophyton, *Sporothrix schenckii*, Aspergillus or Candida.

Therefore, it is an object of the present invention to provide protoberberine salts derivatives which exhibit fungicidal effect and/or growth-inhibitory effect against fungi.

Another object of the present invention is to provide a pharmaceutically available 7,8-dihydroprotoberberine derivative and salt thereof, i.e., reduction product of the above-described protoberberine derivative.

Yet another object of the present invention is to provide a pharmaceutical formulation containing pharmaceutically effective amount of the above protoberberine salts derivative or of its reduction product and salts thereof.

A still further object of the present invention is to provide an antifungal formulation containing pharmaceutically effective amount of the above protoberberine salt derivative or of its reduction product and salts thereof.

A still further object of the present invention is to provide processes for preparing the above-described protoberberine salts derivatives, and its reduction product and salts thereof, i.e., 13-substituted berberine salt and 13-substituted palmatine salt.

The above objects of the present invention are achieved by providing the protoberberine salt derivatives or the following chemical formula (I)

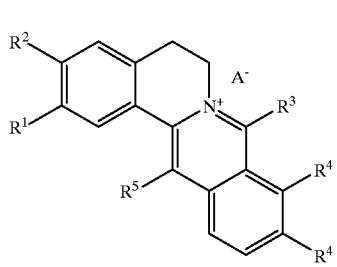

(I)

wherein $R^1$, $R^2$, and $R^4$ may be the same or different, and represent $C_1$–$C_5$ alkoxy, $R^3$ represents hydrogen or $C_1$–$C_{10}$ alkyl, A represents inorganic acid ion, organic acid ion or halide, more particularly, nitrate, sulfate, acetate, tartrate, maleate, succinate, citrate, fumarate, aspartate, salicylate, glycerate, ascorbate, fluoride, chloride, iodide or bromide, $R^5$ represents hydrogen, pyridylmethyl, substituted pyridylmethyl or a group having the following chemical formula (XI)

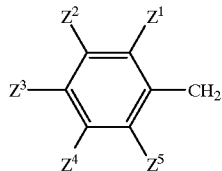
(XI)

wherein $Z^1$, $Z^2$, $Z^3$, $Z^4$ and $Z^5$ may be the same or different, and represent hydrogen, halogen, $C_1$–$C_5$ alkyl, trifluoromethyl, phenyl, substituted phenyl, nitro, $C_1$–$C_4$ alkoxy, $C_1$–$C_4$ alkylamino, acetylamino, $C_1$–$C_8$ trialkyl ammonium, guanidinyl, methylthio, ethylthio, trifluoromethoxy, hydroxy, phenoxy, vinyl, carboxyl and $C_1$–$C_2$ alkoxylcarbonyl groups.

Another object of the present invention is achieved by providing a pharmaceutically available 7,8-dihydroprotoberberine derivative and salts thereof, i.e., the reduction product of the above-described protoberberine derivative of the following chemical formula(II)

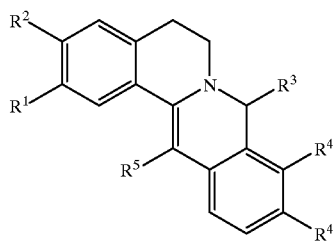
(II)

wherein $R^1$, $R^2$, $R^3$, $R^4$ and $R^5$ are as defined above.

Another object of the present invention is achieved by providing a pharmaceutical formulation which contains pharmaceutically effective amount of the compounds of the above chemical formulae (I) or (II), and contains pharmaceutically allowable excipient or vehicle.

Another object of the present invention is achieved by providing an antifungal formulation which contains pharmaceutically effective amount of the compounds of the above chemical formulae (I) or (II), and contains pharmaceutically allowable excipient or vehicle.

Another object of the present invention is achieved by providing processes for preparing 13-substituted berberine salt or 13-substituted palmatine salt of the following chemical formula (V), in which:

1.0 Mol of berberine salt or palmatine salt of the following chemical formulae (III) is reacted with 1.0 to 3.0 mol of $NaBH_4$ and 2.0 to 4.0 mol of potassium carbonate in alcohol solvent to prepare dihydroberberine or dihydropalmatine of the following chemical formula (VI);

The compound thus obtained is reacted with 1.0 to 3.0 mol of electrophiles ($R^5$-X) in organic solvent to prepare 13-alkyl-dihydroberberine compound or 13-alkyl-dihydropalmatine of the following chemical formula (VII); and The compound thus obtained is oxidized with N-Chlorosuccinimide(NCS) or N-bromosuccinimide to give the above-mentioned 13-substituted berberine salt or 13-substituted palmatine salt.

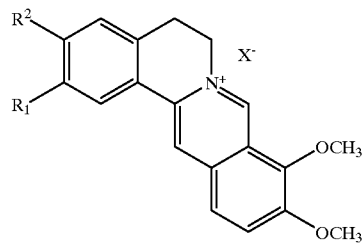
(III)

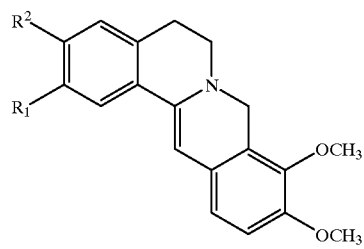
(VI)

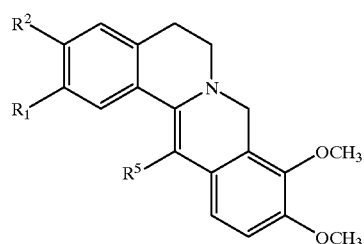
(VII)

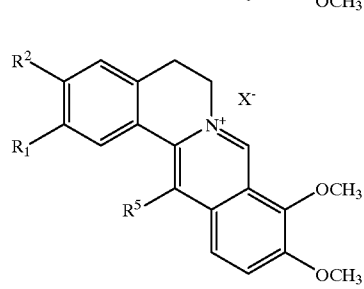
(V)

wherein $R^1$, $R^2$, $R^5$ are as defined above and $X^-$ represents inorganic acid ion, organic acid ion or halide, more particularly, nitrate, sulfate, acetate, tartrate, maleate, succinate, citrate, fumarate, aspartate, salicylate, glycerate, ascorbate, fluoride, chloride, iodide or bromide.

The present invention is further explained hereinbelow.

The present invention provides protoberberine(5.6-dihydro-dibenzo[a,g]quinolizinium) salt derivatives of the above chemical formula (I) and pharmaceutically available 7,8-dihydroprotoberberine tertiary amine derivatives and salt thereof. i.e., the reduction product of the protoberberine derivatives of the above chemical formula (II).

In general, according to the process described in U.K. patent No. 125,627, the novel compounds of the above chemical formulae (I) and (II) of the present invention are prepared from berberine salt or palmatine salt of the following chemical formula (III) by the process of the following reaction scheme(1a).

The following reaction scheme (1a) represents the reaction steps for the preparation of novel protoberberine derivatives, Nos 1 to 6, 15 to 19, 62 to 63, 66 to 77 of the following Table 1, in which:

1.0 Mol of berberine salt or palmatine salt of the above formula (III) is reacted with 3.5 to 11.5 mol of NaOH and 2.5 to 13.5 mol of acetone to obtain 8-acetonyldihydro berberine or 8-acetonyldihydropalmatine of the following chemical formula (IV); and The compound of the following chemical formula (IV) is reacted with 2.5 to 7.5 mol of electrophiles ($R^5$-X) under reflux in organic solvent to obtain 13-alkylberberine salt or 13-alkylpalmatine salt,

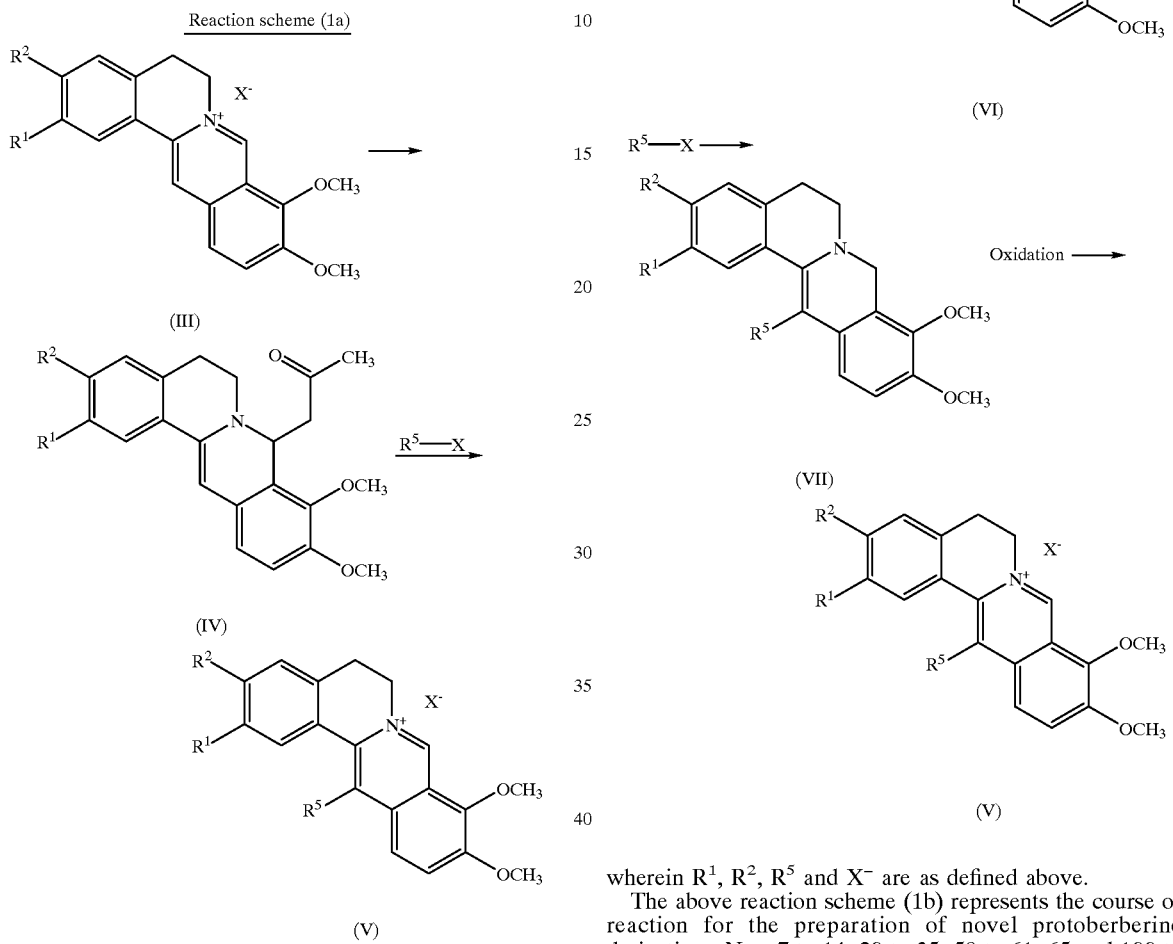

wherein $R^1$, $R^2$, $R^5$ and $X^-$ are as defined above.

The novel compounds having the above chemical formulae I and II of the present invention, may be prepared by processes of the following reaction scheme (1b).

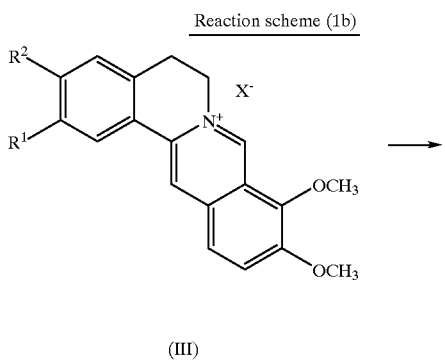

wherein $R^1$, $R^2$, $R^5$ and $X^-$ are as defined above.

The above reaction scheme (1b) represents the course of reaction for the preparation of novel protoberberine derivatives, Nos. 7 to 14, 20 to 35, 58 to 61, 65 and 100 to 102 described in the following Table 1, in which: 1.0 mol of berberine salt or palmatine salt of the following chemical formulae (III) is reacted with 1.0 to 3.0 mol of $NaBH_4$ and 2.0 to 4.0 mol of potassium carbonate in alcohol solvent to prepare dihydroberberine or dihydropalmatine of the following chemical formula (VI); the compound thus obtained is reacted with 1.0 to 3.0 mol of electrophiles ($R^5$-X) in organic solvent to prepare 13-alkyldihydroberberine compound or 13-alkyldihydropalmatine of the following chemical formula (VII); and the compound (VII) thus obtained is oxidized with N-chlorosuccinimide (NCS) or N-bromosuccinimide to give 13-substituted berberine salt or palmatine salt of the chemical formula (V).

The following reaction scheme (1c) represents the course of reaction for the preparation of novel protoberberine derivative No. 85 described in the following Table 1, in which:

1.0 mol of the compound having the chemical formulae (III) or (V) is reacted with 1.5 to 9.5 mol of Lewis acid, for example, anhydrous aluminum chloride in chemical formula (VIII); and the resulting compound is reacted with 4.0 to 15.0 mol of electrophile (R-X) under reflux in organic solvent to obtain protoberberine salt derivatives of the following chemical formula (IX).

Reaction scheme (1c)

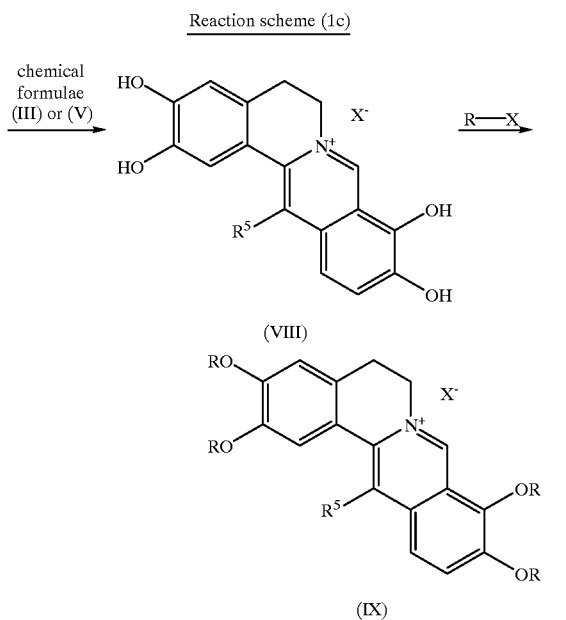

wherein $R^5$ and $X^-$ are as defined above, R represents $C_1$–$C_5$ alkyl.

The following reaction scheme (1d) represents the course of reaction for the preparation of novel protoberberine derivatives, Nos. 89 to 99 and 103 to 115 described in the following Table 1, in which 1.0 mol of the compound having the chemical formulae (V) or (IX) is reacted with 2.0 to 6.0 mol of $LiAlH_4$ or 1.0 to 3.0 mol of $NaBH_4$ and 2.0 to 4.0 mol of potassium carbonate to obtain dihydro protoberberine derivative of the following chemical formula (II).

Reaction scheme (1d)

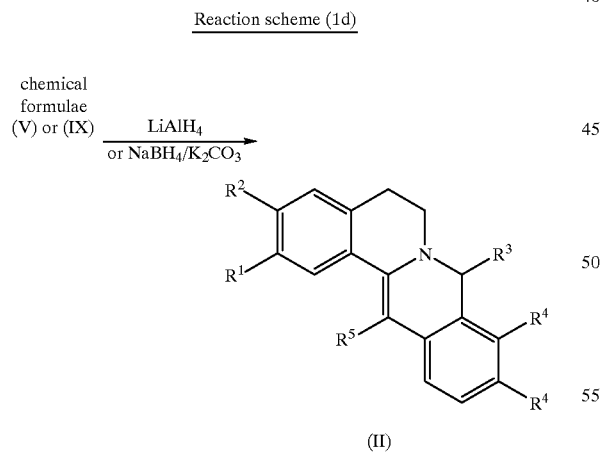

in which $R^1$, $R^2$, $R^3$, $R^4$ and $R^5$ are as defined above.

The following reaction scheme (1e) represents the course of reaction for the preparation of novel protoberberine derivatives, Nos. 116, 117 and 118 described in the following Table 1, in which 1.0 mol of the compound having the chemical formulae (III) or (V) is reacted with 2.0 to 6.0 mol of alkylmagnesiumhalide($R^3$-MgX) to obtain dihydroprotoberberine derivative of the following chemical formula (II)

Reaction scheme (1e)

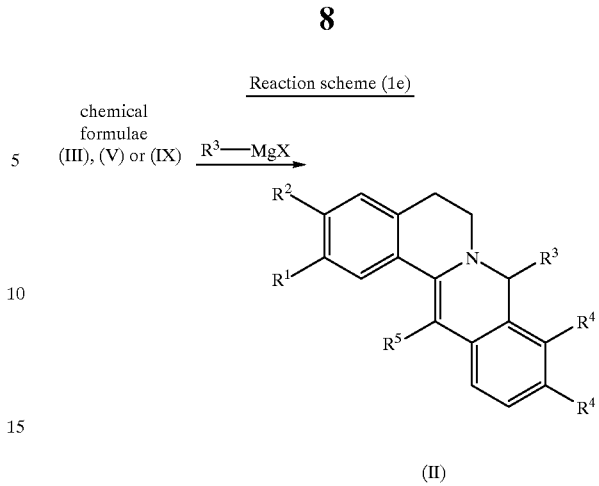

in which $R^1$, $R^2$, $R^3$, $R^4$ and $R^5$ are as defined above.

The following reaction scheme (1f) represents the reaction steps for the preparation of the pharmaceutically available salt of the present invention by the substitution of the counter anion of the quaternary ammonium ion to give novel protoberberine derivatives, Nos. 36, 87 and 88 of the following Table 1, in which 1.0 mol of protoberberine salt of the above formula (III), (V) or (IX) is reacted with 2.5 to 6.5 mol of NaOH and 2.5 to 6.5 mol of acetone to obtain 8-acetonyldihydroprotoberberine and the resulting compound is subsequently treated with inorganic acid or organic acid to substitute anion.

In the following reaction scheme(1f), it is preferable that $A^-$ is inorganic acid ion, organic acid ion or halide, preferably, nitrate, sulfate, acetate, tartrate, maleate, succinate, citrate, fumarate, aspartate, salicylate, glycerate, ascorbate.

Reaction scheme (1f)

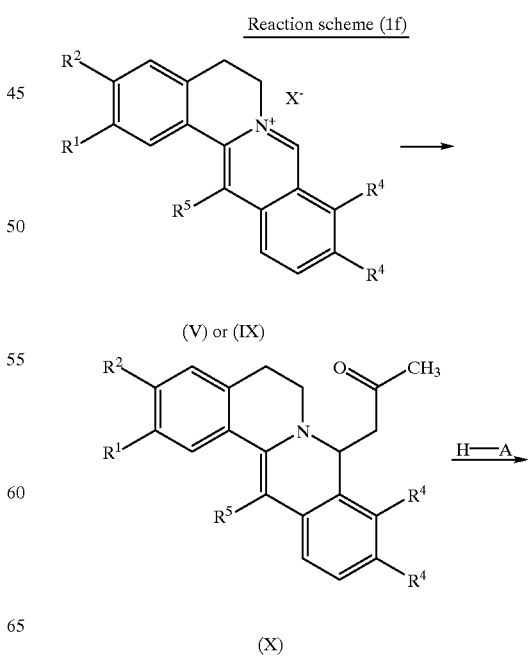

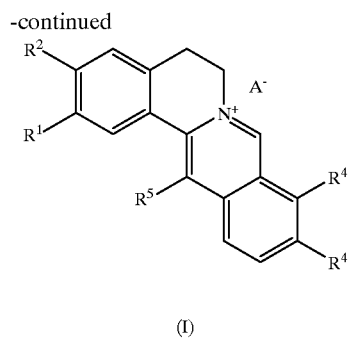

(I)

in which $R^1$, $R^2$, $R^4$ and $R^5$ are as defined above, $R^3$ represents hydrogen, $A^-$ and $X^-$ are different each other and represent inorganic acid ion, organic acid ion or halide, more particularly, nitrate, sulfate, acetate, tartrate, maleate, succinate, citrate, fumarate, aspartate, salicylate, glycerate, ascorbate, fluoride, chloride, iodide or bromide Meanwhile, among the compounds having the above chemical formula (I), the compound wherein $R^1$-$R^2$, $R^3$, $R^4$ and $R^5$ are methylenedioxy(—O—CH$_2$—O—), hydrogen, methoxy and 3,4-dimethyibenzyl respectively, the compound wherein $R^1$-$R^2$, $R^3$, $R^4$ and $R^5$ are methylenedioxy (—O—CH$_2$—O—), hydrogen, methoxy and 4-(tert-butyl) benzyl respectively, the compound wherein $R^1$, $R^2$, $R^3$, $R^4$ and $R^5$ are methoxy, methoxy, hydrogen, methoxy and 4-(tert-butyl)benzyl respectively, the compound wherein $R^1$, $R^2$, $R^3$, $R^4$ and $R^5$ are methoxy, methoxy, hydrogen, methoxy and 4-isopropylbenzyl respectively, the compound wherein $R^1$, $R^2$, $R^3$, $R^4$ and $R^5$ are methoxy, methoxy, hydrogen, methoxy and 4-phenylbenzyl respectively, and the compound wherein $R^1$, $R^2$, $R^3$, $R^4$ and $R^5$ are propoxy, propoxy, hydrogen, propoxy and hydrogen respectively, exhibit preferable pharmaceutical efficacy.

Among the compounds having the above chemical formula (II), the compound wherein $R^1$-$R^2$, $R^3$, $R^4$ and $R^5$ are methylenedioxy(—O—CH$_2$—O—), octyl(—C$_8$H$_{17}$), methoxy and hydrogen respectively, or the compound wherein $R^1$, $R^2$, $R^3$, $R^4$ and $R^5$ are propoxy, propoxy, hydrogen, propoxy and hydrogen respectively, exhibit preferable pharmaceutical efficacy.

According to the present invention, a pharmaceutical formulation and antifungal formulation which comprises pharmaceutically effective amount of the compounds of the above chemical formulae (I) or (II) and pharmaceutically allowable excipient or vehicle, are provided. Such formulations may be prepared to tablet, syrup or ointment, and may also be dosed by oral delivery, injection, vaginal delivery, dermal application. The effective dosage may be varied within the activity range depend on the amount of above excipient or vehicle.

BEST MODE FOR CARRYING OUT THE INVENTION

The present invention will be more specifically illustrated by the following examples but it should be understood that the present invention is not limited to these examples in any manner. The compound number used in the following examples denotes the compound number described in the following Table 1.

EXAMPLE 1

Preparation of 13-benzylberberine iodide(comp. No. 1)

10 G of berberine hydrochloride(an extract of Huanglian, Coptis spp.), 40 ml of water, 10 ml of acetone, 15 ml of 50% agueous NaOH was introduced into a reaction vessel. The reaction mixture was stirred vigorously for 30 minutes. The resulting solid was filtered, washed twice with 10 ml of 80% methanol and then dried to give 8.5 g of 8-acetonylhydroberberine. 5.0 G of 8-acetonylberberine was dissolved in 30 ml of acetonitrile, and 15 ml of benzylchloride and 10 g of NaI were added thereto. The reaction mixture was refluxed for 3 hours and concentrated, and then purified by chromatography over silica gel eluting with methanol/dichloromethane (1:50), to give 3.0 g of 13-benzylberberine iodide.

NMR(300 MHz, DMSO-d$_6$) δ: 3.25(t, 2H), 4.08(s, 3H), 4.17(s, 3H), 4.80(s, 2H), 4.91(t, 2H), 6.17(s, 2H), 6.90(s, 1H), 7.01(m, 2H), 7.10(s, 1H), 7.17(m, 3H), 7.86(d, 1H), 8.17(d, 1H), 10.11(s, 1H)

EXAMPLE 2

Preparation of 13-(4-chlorobenzyl)berberine iodide (comp. No. 2)

5.0 G of 8-acetonylberberine was dissolved in 30 ml of acetonitrile, 16 ml of 4-chlorobenzylchloride, and 10 g of NaI were added thereto. The reaction mixture was refluxed for 3 hours and concentrated. The reaction mixture thus obtained was adsorbed with Celite, and then purified by chromatography over silica gel eluting with methanol/dichloromethanee(1:50) to give 2.7 g of 13-(4-chlorobenzyl) berberine iodide.

NMR(300 MHz, DMSO-d$_6$) δ: 3.21(t, 2H), 4.09(s, 3H), 4.17(s, 3H), 4.80(s, 2H), 4.91(broad t, 2H), 6.17(s, 2H), 6.90(s, 1H), 7.05(d, 2H), 7.17(s, 1H), 7.40(d, 2H), 7.86(d, 1H), 8.17(d, 1H), 9.87(s, 1H)

EXAMPLE 3

Preparation of 13-(3-chlorobenzyl)berberine iodide (comp. No. 3)

The process of Example 2 was repeated except that 3-Chlorobenzyl chloride was employed in place of 4-chlorobenzyl chloride of Example 2, to obtain 2.8 g of 13-(3-chlorobenzyl)berberine iodide.

NMR(300 MHz, DMSO-d$_6$) δ: 3.20(t, 2H), 4.07(s, 3H), 4.17(s, 3H), 4.70(s, 2H), 4.85(broad t, 2H), 6.18(s, 2H), 6.90(s, 1H), 7.12(s, 1H), 7.17(s, 1H), 7.31(t, 1H), 7.40(d, 1H), 7.48(d, 1H), 7.76(d, 1H), 8.10O(d, 1H), 10.05(s, 1H)

EXAMPLE 4

Preparation of 13-(2-chlorobenzyl)berberine iodide (comp. No. 4)

The process of Example 2 was repeated except that 2-chlorobenzyl chloride was employed in place of 4-chlorobenzyl chloride of Example 2 to obtain 2.3 g of 13-(2-chlorobenzyl)berberine iodide.

NMR(300 MHz, DMSO-d$_6$) δ: 3.20(t, 2H), 4.03(s, 3H), 4.13(s, 3H), 4.65(s, 2H), 4.91(broad t, 2H), 6.09(s, 2H), 6.74(s, 1H), 6.80(d, 2H), 7.17(s, 1H), 7.24(t,1H), 7.35(t, 1H), 7.66(d, 1H), 7.70(d, 1H), 8.11(d, 1H), 10.05(s, 1H)

EXAMPLE 5

Preparation of 13-(4-bromobenzyl)berberine iodide (comp. No. 5)

The process of Example 2 was repeated except that 4-Bromobenzyl chloride was employed in place of 4-chlorobenzyl chloride of Example 2 to obtain 2.5 g of 13-(4-bromobenzyl)berberine iodide.

NMR(300 MHz, DMSO-$d_6$) δ: 3.21(t, 2H), 4.09(s, 3H), 4.17(s, 3H), 4.80(s, 2H), 4.91(broad t, 2H), 6.17(s, 2H), 6.91(s, 1H), 7.13(d, 2H), 7.16(s, 1H), 7.55(t, 1H), 7.74(t, 1H), 8.11(d, 1H), 10.05(s, 1H)

EXAMPLE 6

Preparation of 13-(3-bromobenzyl)berberine iodide (comp. No. 6)

The process of Example 2 was repeated except that 3-Bromobenzyl chloride was employed in place of 4-chlorobenzyl chloride of Example 2 to obtain 2.8 g of 13-(3-bromobenzyl)berberine iodide.

NMR(300 MHz, DMSO-$d_6$) δ: 3.20(t, 2H), 4.07(s, 3H), 4.17(s, 3H), 4.70(s, 2H), 4.85(broad t, 2H), 6.10(s, 2H), 6.91(s, 1H), 7.15(d, 2H), 7.17(s, 1H), 7.31(t, 1H), 7.48(d, 1H), 7.50(d, 1H), 7.76(d, 1H), 8.09(d, 1H), 10.02(s, 1H)

EXAMPLE 7

Preparation of 13-(2,3-dichlorobenzyl)berberine chloride(comp. No.7)

To a solution of 9.27 g (20 mmol) of berberine hydrochloride(an extract of Huanglian, Coptis spp.) in 250 ml of methanol was added to 8.29 g(60 mol) of $K_2CO_3$ and then 0.24 g(6.4mmol) of $NaBH_4$ was slowly added thereto. The reaction was proceeded for 4 hours at 0° C. The reaction mixture was concentrated and then the solid thus obtained was filtered, washed successively with 50 ml of distilled water until it become to be neutral and dried under vacuo to give 6.61 g of 8-dihydroberberine(yield: 98%). A mixture of 2.70 g(18 mmol) of NaI and 4.32 g(18 mmol) of 2,3-dichlorobenzyl bromide in 150 ml of acetonitrile was stirred at room temperature for 1 hour and then 5.06 g(15 mmol) of 8-dihydroberberine obtained in the above, was added to the reaction mixture and heated for 3 hours under reflux. The reaction mixture was concentrated and dissolved in 100 ml of chloroform and then quenched with 10% aqueous solution of $K_2CO_3$ to separate organic layer. The organic layer thus separated was dried over $MgSO_4$ and filtered. The filtrate was concentrated to an extent of 100 ml and 2.60 g(18 mmol) of NCS (N-chlorosuccinimide) was added thereto. The reaction was proceeded at room temperature for 1 hour. The reaction mixture was washed with 100 ml of distilled water. The organic layer was separated and dried over $MgSO_4$ and filtered. The filtrate was concentrated. The solid thus obtained was triturated in 20 ml of diethylether and filtered to give 4.20 g of 13-(2,3-dichlorobenzyl) berberine chloride. (Melting point: 116° C.)

NMR(300 MHz, $CDCl_3$) δ: 3.24–3.28(broad t, J=5.7 Hz, 2H), 4.04(s, 3H), 4.42(s, 3H), 4.68(s, 2H), 5.20–5.24(broad t, J=5.7 Hz, 2H), 6.04(s, 2H), 6.74–6.77(m, 2H), 6.90(s, 1H), 7.11–7.16(t,J=8.1 Hz, 1H), 7.41–7.49(m, 2H), 7.73–7.70(d, J=9.3 Hz, 1H), 10.55(s, 1H)

EXAMPLE 8

Preparation of 13-(2-fluorobenzyl)berberine chloride(comp. No. 8)

NaI(2.70 g, 18 mmol) was dissolved in 150 ml of acetonitrile and then 2.60 g (18 mmol) of 2-fluorobenzyl chloride was added thereto and reacted at room temperature for 1 hour. 8-Dihydroberberine (5.068 g, 15 mmol) was added to the resulting solution and the mixture was heated under reflux for 3 hours. The reaction mixture thus obtained was concentrated and dissolved in 100 ml of chloroform and then quenched with 10% aqueous solution of $K_2CO_3$ to separate organic layer. The organic layer thus separated was dried over $MgSO_4$ and filtered. The filtrate was concentrated to an extent of 100 ml and 2.60 g (18 mmol) of NCS (N-chlorosuccinimide) was added thereto and reacted at room temperature for 1 hour. The reaction mixture was washed with 100 ml of distilled water. The organic layer was separated and dried over $MgSO_4$ and filtered. The filtrate was concentrated. The solid thus obtained was triturated in 20 ml of diethylether and filtered to give 4.06 g of 13-(2-fluorobenzyl)berberine chloride. (Melting point: 177° C.)

NMR(300 MHz, $CDCl_3$) δ: 3.23–3.27(broad t, J=5.7 Hz, 2H), 4.03(s, 3H), 4.41(s, 3H), 4.63(s, 2H), 5.36–5.40(broad t, J=5.7 Hz, 2H), 6.02(s, 2H), 6.71–6.77(m, 1H), 6.87(s, 1H), 6.90(s, 1H), 7.02–7.07(m, 1H), 7.20–7.36(m, 2H), 7.54–7.57(d, J=9.3 Hz, 1H), 7.69–7.72(d, J=9.3 Hz, 1H), 10.88(s, 1H)

EXAMPLE 9

Preparation of 13-(2-chloro-6-fluorobenzyl) berberine chloride(comp. No. 9)

The process of Example 8 was repeated except that 2-chloro-6-fluorobenzyl chloride was employed in place of 2-fluorobenzyl chloride of Example 8 to give 3.98 g of 13-(2-chloro-6-fluorobenzyl)berberine chloride. (Melting point: 80° C.)

NMR(300 MHz, $CDCl_3$) δ: 3.26–3.30(broad t, J=5.7 Hz, 2H), 4.03(s, 3H), 4.32(s, 3H), 4.89(s, 2H), 5.05–5.09(broad t, J=5.7 Hz, 2H), 6.09(s, 2H), 6.88–6.91(m, 1H), 6.94(s, 1H), 7.10(s, 1H), 7.18–7.24(m, 2H), 7.72(s, 2H), 10.11(s, 1H)

EXAMPLE 10

Preparation of 13-(2,6-difluorobenzyl)berberine chloride(comp. No. 10)

The process of Example 8 was repeated except that 2,6-difluorobenzyl chloride was employed in place of 2-fluorobenzyl chloride of Example 8 to give 4.11 g of 13-(2,6-difluorobenzyl)berberine chloride. (Melting point: 94° C.)

NMR(300 MHz, $CDCl_3$) δ: 3.26–3.30(broad t, J=5.7 Hz, 2H), 4.04(s, 3H), 4.32(s, 3H), 4.80(s, 2H), 5.14–5.18(broad t, J=5.7 Hz, 2H), 6.09(s, 2H), 6.83–6.88(t, J=8.4 Hz, 2H), 6.95(s, 1H), 7.11(s, 1H), 7.19–7.26(m, 1H), 7.73–7.76(d, J=9.3 Hz, 1H), 7.77–7.80(d, J=9.3 Hz, 1H), 10.18(s, 1H)

EXAMPLE 11

Preparation of 13-(3,4-difluorobenzyl)berberine chloride(comp. No. 11)

The process of Example 8 was repeated except that 3,4-difluorobenzyl chloride was employed in place of 2-fluorobenzyl chloride of Example 8 to give 4.07 g of 13-(3,4-difluorobenzyl)berberine chloride. (Melting point: 88° C.)

NMR(300 MHz, $CDCl_3$) δ: 3.25–3.29(broad t, J=5.7 Hz, 2H), 4.03(s, 3H), 4.29(s, 3H), 4.63(s, 2H), 5.03–5.07(broad t,J=5.7 Hz, 2H), 6.03(s, 2H), 6.84(s, 1H), 6.88(s, 1H), 7.08–7.10(m, 1H), 7.51–7.54(d,J=9.3 Hz, 1H), 7.69–7.74 (m, 3H), 10.52(s, 1H)

EXAMPLE 12

Preparation of 13-(4-fluoro-2-trifluoromethylbenzyl) berberine chloride(comp. No. 12)

The process of Example 8 was repeated except that 4-fluoro-2-trifluoromethylbenzyl chloride was employed in place of 2-fluorobenzyl chloride of Example 8 to give 4.31 g of 13-(4-fluoro-2-trifluoromethylbenzyl)berberine chloride. (Melting point: 127° C.)

NMR(300 MHz, CDCl$_3$) δ: 3.25–3.29(broad t, J=5.7 Hz, 2H), 4.05(s, 3H), 4.36(s, 3H), 4.80(s, 2H), 5.14–5.18(broad t, J=5.7 Hz, 2H), 6.03(s, 2H), 6.78(s, 1H), 6.90(s, 1H), 7.01–7.06(m, 1H), 7.15–7.22(m, 1H), 7.47–7.50(d, J=9.6 Hz, 1H), 7.55–7.60(dd, J=2.7, 9.0 Hz, 1H), 7.73–7.76(d, J=9.6 Hz, 1H), 10.28(s, 1H)

EXAMPLE 13

Preparation of 13-(2,3,4,5,6-pentafluorobenzyl) berberine chloride (comp. No. 13)

The process of Example 8 was repeated except that 2,3,4,5,6-pentafluorobenzyl chloride was employed in place of 2-fluorobenzyl chloride of Example 8 to give 4.14 g of 13-(2,3,4,5,6-pentafluorobenzyl)berberine chloride. (Melting point: 95° C.)

NMR(300 MHz, CDCl$_3$) δ: 3.26–3.30(broad t, J=5.7 Hz, 2H), 4.07(s, 3H), 4.32(s, 3H), 4.89(s, 2H), 4.97–5.01(broad t, J=5.7 Hz, 2H), 6.1 l(s, 2H), 6.96(s, 1H), 7.09(s, 1H), 7.70–7.74(d, J=9.6 Hz, 1H), 7.81–7.85(d, J=9.6 Hz, 1H), 10.01(s, 1H)

EXAMPLE 14

Preparation of 13-(2,3,5,6-tetrafluoro-4-trifluoromethylbenzyl) berberine chloride (comp. No. 14)

The process of Example 8 was repeated except that 2,3,5,6-tetrafluoro-4-trifluoromethylbenzyl chloride was employed in place of 2-fluorobenzyl chloride of Example 8 to give 4.36 g of 13-(2,3,5,6-tetrafluoro-4-trifluoromethylbenzyl) berberine chloride. (Melting point: 150° C.)

NMR(300 MHz, CDCl$_3$) δ: 3.23–3.27(broad t, J=5.7 Hz, 2H), 4.07(s, 3H), 4.35(s, 3H), 4.93(s, 2H), 5.17–5.21(broad t,J=5.7 Hz, 2H), 6.11(s, 2H), 6.97(s, 1H), 7.01(s, 1H), 7.62–7.65(d, J=9.0 Hz, 1H), 7.81–7.84(d, J=9.0 Hz, 1H), 10.51(s, 1H)

EXAMPLE 15

Preparation of 13-(4-methylbenzyl)berberine chloride(comp. No. 15)

4-Methylbenzyl chloride, instead of 4-chlorobenzyl chloride of Example 2, was treated by the process described in Example 2 to give 2.2 g of 13-(4-methyl benzyl)berberine chloride.

NMR(300 MHz, DMSO-d$_6$) δ: 2.23(s, 3H), 3.21(t, 2H), 4.09(s, 3H), 4.17(s, 3H), 4.60(s, 2H), 4.82(broad t, 2H), 6.05(s, 2H), 6.97(s, 2H), 7.06(d, 2H), 7.17(s, 1H), 7.18(d, 2H), 7.82(d, 1H), 8.25(d, 1H), 10.05(s, 1H)

EXAMPLE 16

Preparation of 13-(3-methylbenzyl)berberine chloride(comp. No. 16)

3-Methylbenzyl chloride, instead of 4-chlorobenzyl chloride of Example 2, was treated by the process described in Example 2 to give 2.10 g of 13-(3-methylbenzyl)berberine chloride.

NMR(300 MHz, DMSO-d$_6$) δ: 2.27(s, 3H), 3.20(t, 2H), 4.03(s, 3H), 4.13(s, 3H), 4.70(s, 2H), 4.95(broad t, 2H), 6.09(s, 2H), 6.92(d, 1H), 7.00(s, 2H), 7.07(d, 1H), 7.11(d, 1H), 7.18(s, 1H), 7.24(t, 1H), 7.76(d, 1H), 8.10(d, 1H), 10.05(s, 1H)

EXAMPLE 17

Preparation of 13-(2-methylbenzyl)berberine chloride(comp. No. 17)

2-Methylbenzyl chloride, instead of 4-chlorobenzyl chloride of Example 2, was treated by the process described in Example 2 to give 2.5 g of 13-(2-methyl benzyl)berberine chloride.

NMR(300 MHz, DMSO-d$_6$) δ: 2.25(s, 3H), 3.18(t, 2H), 4.05(s, 3H), 4.17(s, 3H), 4.55(s, 2H), 4.95(broad t, 2H), 6.05(s, 2H), 6.61(d, 1H), 6.79(s, 2H), 7.06(t, 1H), 7.16(s, 1H), 7.22(t, 1H), 7.40(d, 1H), 7.72(d, 1H), 8.11(d, 1H), 10.05(s, 1H)

EXAMPLE 18

Preparation of 13-(3,4-dimethylbenzyl)berberine chloride(comp. No. 18)

3,4-Dimethylbenzyl chloride, instead of 4-chlorobenzyl chloride of Example 2, was treated by the process described in Example 2 to give 2.7 g of 13-(3,4-dimethylbenzyl) berberine chloride.

NMR(300 MHz, DMSO-d$_6$) δ: 2.18(s, 3H), 2.20(s, 3H), 3.21(t, 2H), 4.02(s, 3H), 4.13(s, 3H), 4.65(s, 2H), 4.91(broad t, 2H), 6.08(s, 2H), 6.81(d, 1H), 7.01(s, 1H), 7.02(d, 1H), 7.10(d, 1H), 8.11(d, 1H), 10.05(s, 1H)

EXAMPLE 19

Preparation of 13-(2,4-dimethylbenzyl)berberine chloride(comp. No. 19)

2,4-Dimethylbenzyl chloride, instead of 4-chlorobenzyl chloride of Example 2, was treated by the process described in Example 2 to give 2.4 g of 13-(2,4-dimethylbenzyl) berberine chloride.

NMR(300 MHz, DMSO-d$_6$) δ: 2.27(s, 3H), 2.42(s, 3H), 3.20(t, 2H), 4.07(s, 3H), 4.17(s, 3H), 4.50(s, 2H), 4.90(broad t, 2H), 6.08(d, 1H), 6.50(d, 1H), 6.81(s, 1H), 6.88(dd, 1H), 7.16(s, 1H), 7.21(s, 1H), 8.27(d, 1H), 10.05(s, 1H)

EXAMPLE 20

Preparation of 13-(2.5-dimethylbenzyl)berberine chloride(comp. No. 20)

2,5-Dimethylbenzyl chloride, instead of 2-fluorobenzyl chloride of Example 8, was treated by the process described in Example 8 to give 4.31 g of 13-(2,5-dimethylbenzyl) berberine chloride. (Melting point: 79° C.)

NMR(300 MHz, CDCl$_3$) δ: 2.14(s, 3H), 2.41(s, 3H), 3.22–3.26(broad t, J=5.7 Hz, 2H), 4.06(s, 3H), 4.37(s, 3H), 4.48(s, 2H), 5.06–5.10(broad t, J=5.7 Hz, 2H), 6.01(s, 2H), 6.45–6.46(d, J=2.1 Hz, 1H), 6.89(s, 1H), 6.90(s, 1H), 7.04–7.06(dd, J=2.1, 7.8 Hz, 1H), 7.24–7.26(d, J=7.8 Hz, 1H), 7.56–7.60(d, J=9.3 Hz, 1H), 7.71–7.75(d, J=9.3 Hz, 1H), 10.18(s, 1H)

EXAMPLE 21

Preparation of 13-(5-methyl-2-nitrobenzyl)berberine chloride(comp. No. 21)

5-Methyl-2-nitrobenzyl chloride, instead of 2-fluorobenzyl chloride of Example 8, was treated by the process described in Example 8 to give 4.20 g of 13-(5-methyl-2-nitrobenzyl)berberine chloride. (Melting point: 145° C.)

NMR(300 MHz, CDCl$_3$) δ: 2.35(s, 3H), 3.23–3.27(broad t, J=5.7 Hz, 2H), 4.06(s, 3H), 4.37(s, 3H), 5.02(s, 2H), 5.01–5.04(broad t, J=5.7 Hz, 2h), 6.02(s, 2H), 6.84(s, 1H), 6.89(s, 1H), 6.98–6.99(d, J=2.1 Hz, 1H), 7.29–7.32(dd, J=2.1, 8.4 Hz, 1H), 7.49–7.53(d, J=9.3 Hz, 1H), 7.74–7.77 (d, J=9.3 Hz, 1H), 8.16–8.19(d, J =8.4 Hz, 1H), 9.99(s, 1H)

EXAMPLE 22

Preparation of 13-(4-methyl-3-nitrobenzyl)berberine chloride(comp. No. 22)

4-Methyl-3-nitrobenzyl chloride, instead of 2-fluorobenzyl chloride of Example 8, was treated by the process described in Example 8 to give 4.13 g of 13-(4-methyl-3-nitrobenzyl)berberine chloride. (Melting point: 134° C.)

NMR(300 MHz, CDCl$_3$) δ: 2.61(s, 3H), 3.33–3.37(broad t, J=5.7 Hz, 2H), 4.06(s, 3H), 4.35(s, 3H), 4.80(s, 2H), 4.98–5.02(broad t, J=5.7 Hz, 2H), 6.04(s, 2H), 6.87(s, 1H), 6.91(s, 1H), 7.26–7.40(m, 2H), 7.58–7.61(d, J=9.0 Hz, 1H), 7.75–7.78(m, 2H), 9.99(s, 1H)

EXAMPLE 23

Preparation of 13-(2-methyl-3-nitrobenzyl)berberine chloride(comp. No. 23)

2-Methyl-3-nitrobenzyl chloride, instead of 2-fluorobenzyl chloride of Example 8, was treated by the process described in Example 8 to give 3.91 g of 13-(2-methyl-3-nitrobenzyl)berberine chloride. (Melting point: 116° C.)

NMR(300 MHz, CDCl$_3$) δ: 2.59(s, 3H), 3.26–3.30(broad t, J=5.7 Hz, 2H), 4.06(s, 3H), 4.37(s, 3H), 4.62(s, 2H), 5.18–5.22(broad t, J=5.7 Hz, 2H), 6.03(s, 2H), 6.72(s, 1H), 6.91(s, 1H), 7.01–7.03(d, J=7.5 Hz, 1H), 7.23–7.26(d, J=8.1 Hz, 1H), 7.43–7.46(d,J=9.3 Hz, 1H), 7.72–7.78(t,J=7.5 Hz, 2H), 10.41(s, 1H)

EXAMPLE 24

Preparation of 13-(2-trifluoromethylbenzyl)berberine chloride(comp. No. 24)

2-Trifluoromethylbenzyl chloride, instead of 2-fluorobenzyl chloride of Example 8, was treated by the process described in Example 8 to give 3.83 g of 13-(2-trifluoromethylbenzyl)berberine chloride. (Melting point: 141° C.)

NMR(300 MHz, CDCl$_3$) δ: 3.28–3.32(broad t, J=5.7 Hz, 2H), 4.04(s, 3H), 4.36(s, 3H), 4.85(s, 2H),5.16–5.20(broadt, J=5.7 Hz, 2H), 6.01(s, 2H), 6.81(s, 1H), 6.90(s, 1H), 6.98–7.02(m, 1H), 7.45–7.52(m, 3H), 7.71–7.74(d,J=9.6 Hz, 1H), 7.84–7.88(m, 1H), 10.28(s, 1H)

EXAMPLE 25

Preparation of 13-(3-trifluoromethylbenzyl)berberine chloride(comp. No. 25)

3-Trifluoromethylbenzyl chloride, instead of 2-fluorobenzyl chloride of Example 8, was treated by the process described in Example 8 to give 4.09 g of 13-(2-trifluoromethylbenzyl)berberine chloride. (Melting point: 149° C.)

NMR(300 MHz, CDCl$_3$) δ: 3.31–3.35(broad t, J=5.7 Hz, 2H), 4.06(s, 3H), 4.37(s, 3H), 4.81(s,2H), 5.07–5.11(broad t,J=5.7 Hz, 2H), 6.03(s, 2H), 6.85(s, 1H), 6.92(s, 1H), 7.30–7.60(m, 5H), 7.74–7.77(d,J=9.3 Hz, 1H), 10.19(s, 1H)

EXAMPLE 26

Preparation of 13-(4-trifluoromethylbenzyl) berberine chloride(comp. No. 26)

4-Trifluoromethylbenzyl chloride, instead of 2-fluorobenzyl chloride of Example 8, was treated by the process described in Example 8 to give 4.27 g of 13-(4-trifluoromethylbenzyl)berberine chloride. (Melting point: 168° C.)

NMR(300 MHz, CDCl$_3$) δ: 3.31–3.35(broad t, J=5.7 Hz, 2H), 4.05(s, 3H), 4.36(s, 3H), 4.81(s, 2H), 5.05–5.09(broad t,J=5.7 Hz, 2H), 6.03(s, 2H), 6.86(s, 1H), 6.91(s, 1H), 7.29–7.32(d, J=8.4 Hz, 2H), 7.55–7.58(d, J=9.3 Hz, 1H), 7.63–7.66(d, J=8.4 Hz, 2H), 7.73–7.76(d, J=9.3 Hz, 1H), 10.20(s, 1H)

EXAMPLE 27

Preparation of 13-(4-methoxybenzyl)berberine chloride(comp. No.27)

4-Methoxybenzyl chloride, instead of 2-fluorobenzyl chloride of Example 8, was treated by the process described in Example 8 to give 4.38 g of 13-(4-methoxybenzyl) berberine chloride. (Melting point: 214° C.)

NMR(300 MHz, CDCl$_3$) δ: 3.23–3.27(broad t, J=5.7 Hz, 2H), 3.81(s, 3H), 4.03(s, 3H), 4.43(s, 3H), 4.61(s, 2H), 5.17–5.22(broad t,J=5.7 Hz, 2H), 6.01(s, 2H), 6.889(s, 1H), 6.88–6.91(d, J=9.0 Hz, 2H), 7.00(s, 1H), 7.02–7.05(d, J=9.0 Hz, 2H), 7.62=7.65(d, J=8.4 Hz, 1H), 7.68–7.71(d, J=8.4H, 1H), 10.44(s, 1H)

EXAMPLE 28

Preparation of 13-(3-methoxybenzyl)berberine chloride(comp. No. 28)

3-Methoxybenzyl chloride, instead of 2-fluorobenzyl chloride of Example 8, was treated by the process described in Example 8 to give 4.30 g of 13-(3-methoxybenzyl) berberine chloride. (Melting point: 72° C.)

NMR(300 MHz, CDCl$_3$) δ: 3.30–3.34(broad t, J=5.7 Hz, 2H), 3.79(s, 3h), 4.04(s, 3H), 4.37(s, 3H), 4.68(s, 2H), 5.13–5.17(broad t, J=5.7 Hz, 2H), 6.02(s, 2H), 6.68–6.70(m, 2H), 6.83–6.86(m, 1H), 6.90(s, 1H), 7.01(s, 1H), 7.29–7.32 (m, 1H), 7.65–7.68(d, J=9.3 Hz, 1H), 7.71–7.74(d, J=9.3 Hz, 1H), 10.34(s, 1H)

EXAMPLE 29

Preparation of 13-(3,4,5-trimethoxabenzyl)berberine chloride(comp. No. 29)

3,4,5-Trimethoxybenzyl chloride, instead of 2-fluorobenzyl chloride of Example 8, was treated by the process described in Example 8 to give 4.02 g of 13-(3,4,5-trimethoxybenzyl)berberine chloride. (Melting point: 74° C.)

NMR(300 MHz, CDCl$_3$) δ: 3.23–3.27(broad t, J=5.7 Hz, 2H), 3.75(s, 6H), 3.87(s, 3H), 4.06(s, 3H), 4.35(s, 3H), 4.65(s, 2H), 5.12–5.16(broad t,J=5.7 Hz, 2H), 6.03(s, 2H), 6.34(s, 2H), 6.92(s, 1H), 7.10(s, 1H), 7.68–7.71(d, J=9.0 Hz, 1H), 7.77–7.80(d, J=9.0 Hz, 1H), 10.26(s, 1H)

EXAMPLE 30

Preparation of 13-(4,5-dimethoxy-2-nitrobenzyl) berberine chloride (comp. No. 30)

4,5-Dimethoxy-2-nitrobenzyl chloride, instead of 2-fluorobenzyl chloride of Example 8, was treated by the process described in Example 8 to give 3.89 g of 13-(4,5-dimethoxy-2-nitrobenzyl)berberine chloride. (Melting point: 114° C.)

NMR(300 MHz, CDCl$_3$) δ: 3.11–3.15(broad t, J=5.7 Hz, 2H), 3.67(s, 3H), 4.00(s, 3H), 4.05(s, 3H), 4.36(s, 3H), 5.05(s, 2H), 5.10–5.14(broad t,J=5.7 Hz, 2H), 6.03(s, 2H), 6.47(s, 1H), 6.87(s, 1H), 6.89(s, 1H), 7.48–7.51(d,J=9.3 Hz, 1H), 7.72–7.75(d, J=9.3 Hz, 1H), 7.87(s, 1H), 10.15(s, 1H)

EXAMPLE 31

Preparation of 13-(4-trifluoromethoxybenzyl) berberine chloride(comp. No. 31)

4-Trifluoromethoxybenzyl chloride, instead of 2-fluorobenzyl chloride of Example 8, was treated by the process described in Example 8 to give 4.08 g of 13-(4-trifluoromethoxybenzyl)berberine chloride. (Melting point: 132–134° C.)

NMR(300 MHz, CDCl$_3$) δ: 3.22–3.26(broad t, J=5.7 Hz, 2H), 4.03(s, 3H), 4.37(s, 3H), 4.69(s, 2H), 5.30–5.34(broad t,J=5.7 Hz, 2H), 6.02(s, 2H), 6.86(s, 1H), 6.89(s, 1H), 7.15–7.17(d, J=8.1 Hz, 2H), 7.22–7.24(d, J=8.1 Hz, 2H), 7.55–7.58(d, J=9.3 Hz, 1H), 7.71–7.75(d, J=9.3 Hz, 1H), 10.77(s, 1H)

EXAMPLE 32

Preparation of 13-(2-methoxy-5-nitrobenzyl) berberine chloride(comp. No. 32)

2-Methoxy-5-nitrobenzyl chloride, instead of 2-fluorobenzyl chloride of Example 8, was treated by the process described in Example 8 to give 4.15 g of 13-(2-methoxy-5-nitrobenzyl)berberine chloride. (Melting point: 102° C.)

NMR(300 MHz, CDCl$_3$) δ: 3.38–3.42(broad t, J=5.7 Hz, 2H), 4.06(s, 3H), 4.10(s, 3H), 4.35(s, 3H), 4.66(s, 2H), 5.00–5.04(broadt,J=5.7 Hz, 2H), 6.03(s, 2H), 6.77(s, 1H), 6.92(s, 1H), 7.12–7.15(d, J=9.3 Hz, 1H), 7.52–7.56(m, 2H), 7.75–7.78(d, 9.3 Hz, 1H), 8.26–8.31(dd, J=2.7, 9.6 Hz, 1H), 9.99(s, 1H)

EXAMPLE 33

Preparation of 13-(2-nitrobenzyl)berberine chloride (comp. No. 33)

2-Nitrobenzyl chloride, instead of 2-fluorobenzyl chloride of Example 8, was treated by the process described in Example 8 to give 3.82 g of 13-(2-nitrobenzyl) berberine chloride. (Melting point: 78° C.)

NMR(300 MHz, CDCl$_3$) δ: 3.11–3.15(broad t, J=5.7 Hz, 2H), 4.05(s, 3H), 4.33(s, 3H), 4.99(s, 2H), 5.01–5.05(broad t, J=5.7 Hz, 2H), 6.02(s, 2H), 6.80(s, 1H), 6.90(s, 1H), 7.20–7.80(m, 4H), 8.06–8.09(d, J=9.0 Hz, 1H), 8.20–8.23(d, J=9.0 Hz, 1H), 10.05(s, 1H)

EXAMPLE 34

Preparation of 13-(2-hydroxy-5-nitrobenzyl) berberine chloride(comp. No. 34)

2-Hydroxy-5-nitrobenzyl chloride, instead of 2-fluorobenzyl chloride of Example 8, was treated by the process described in Example 8 to give 3.90 g of 13-(2-hydroxy-5-nitrobenzyl)berberine chloride. (Melting point: 146–147° C.)

NMR(300 MHz, DMSO-d$_6$) δ: 3.14–3.18(broad t, J=5.7 Hz, 2H), 4.05(s, 3H), 4.15(s, 3H), 4.56(s, 2H), 4.88–4.92 (broad t, J=5.7 Hz, 2H), 6.10(s, 2H), 6.85(s, 1H), 7.18(s, 1H), 7.22–7.25(d, J=9.3 Hz, 1H), 7.51–7.52(d, J=2.7 Hz, 1H), 7.75–7.79(d, J=9.3 Hz, 1H), 8.11–8.14(m, 2H), 10.08 (s, 1H), 11.90(s, 1H)

EXAMPLE 35

Preparation of 13-(4-phenylbenzyl)berberine chloride(comp. No. 35)

4-Phenylbenzyl chloride, instead of 2-fluorobenzyl chloride of Example 8, was treated by the process described in Example 8 to give 4.10 g of 13-(4-phenylbenzyl)berberine chloride. (Melting point: 170–172° C.)

NMR(300 MHz, CDCl$_3$) δ: 3.28–3.32(broad t, J=6.0 Hz, 2H), 4.05(s, 3H), 4.36(s, 3H), 4.78(s, 2H), 5.06–5.10(broad t,J=6.0 Hz, 2H), 6.02(s, 2H), 6.90(s, 1H), 7.05(s, 1H), 7.20–7.60(m, 9H), 7.70–7.73(d, J=9.0 Hz, 1H), 7.74–7.78(d, J=9.0 Hz, 1H), 10.14(s, 1H)

EXAMPLE 36

Preparation of 13-(4-(N,N-dimethylamino)benzyl) berberine cloride(comp. No. 36)

(N,N-dimethylamino)benzyl chloride, instead of 2-fluorobenzyl chloride of Example 8, was treated by the process described in Example 8 to give 4.53 g of 13-(4-(N, N-dimethylamino)benzyl)berberine chloride. (Melting point: 152° C.)

EXAMPLE 37

Preparation of N'-methylammonium iodide(comp. No. 37) of 13-(4-(N,N-dimethylamino)benzyl) berberine chloride 4-Chloromethylphenyltrimethylammonium iodide, instead of 2-fluorobenzyl chloride of Example 8, was treated by the process described in Example 8 to give 4.27 g of N'-methylammonium iodide of 13-(4(N,N-dimethylamino) benzyl) berberine chloride. (Melting point: 167° C.)

EXAMPLE 38

Preparation of N'-ethylammonium iodide(comp. No. 38) of 13-(4-(N,N-dimethylamino)benzyl) berberine chloride (4-Chloromethylphenyl)dimethylethylammonium iodide, instead of 2-fluorobenzyl chloride of Example 8, was treated by the process described in Example 8 to give 4.30 g of N'-ethylammonium iodide of 13-(4-(N,N-dimethylamino) benzyl)berberine chloride. (Melting point: 167° C.)

EXAMPLE 39

Preparation of N'-benzylammonium chloride(comp. No. 39) of 13-(4-(N,N-dimethylamino)benzyl) berberine chloride (4-Chloromethylphenyl)benzyldimethylammonium chloride, instead of 2-fluorobenzyl chloride of Example 8, was treated by the process described in Example 8 to give 4.41 g of N'-benzylammonium chloride of 13-(4-(N,N-dimethylamino)benzyl)berberine chloride. (Melting point: 178° C.)

EXAMPLE 40

Preparation of N'-hexylammonium iodide(comp. No. 40) of 13-(4-(N,N-dimethylamino)benzyl) berberine chloride (4-Chloromethylphenyl)dimethylhexylammonium iodide, instead of 2-fluorobenzyl chloride of Example 8, was treated by the process described in Example 8 to give 4.38 g of N'-hexylammonium iodide of 13-(4-(N,N-dimethylamino)benzyl)berberine chloride. (Melting point: 165° C.)

EXAMPLE 41

Preparation of 13-(2-fluoro-4-t-butylbenzyl) berberine chloride(comp. No. 41)

2-Fluoro-4-t-butylbenzyl chloride, instead of 2-fluorobenzyl chloride of Example 8, was treated by the process described in Example 8 to give 4.53 g of 13-(2-fluoro-4-t-butylbenzyl)berberine chloride. (Melting point: 154° C.)

EXAMPLE 42

Preparation of 13-(2-nitro-4-t-butylbenzyl)berberine chloride(comp. No. 42)

2-Nitro-4-t-butylbenzyl chloride, instead of 2-fluorobenzyl chloride of Example 8, was treated by the process described in Example 8 to give 4.03 g of 13-(2-nitro-4-t-butylbenzyl)berberine chloride. (Melting point: 128° C.)

EXAMPLE 43

Preparation of 13-(2-guanidinylbenzyl)berberine chloride(comp. No. 43)

4-Guanidinylbenzyl chloride, instead of 2-fluorobenzyl chloride of Example 8, was treated by the process described in Example 8 to give 4.11 g of 13-(2-guanidinylbenzyl) berberine chloride. (Melting point: 135° C.)

EXAMPLE 44

Preparation of 13-(4-acetylaminobenzyl)berberine chloride(comp. No. 44)

4-Acetylaminobenzyl chloride, instead of 2-fluorobenzyl chloride of Example 8, was treated by the process described in Example 8 to give 4.20 g of 13-(4-acetylaminobenzyl) berberine chloride. (Melting point: 105 ° C.)

EXAMPLE 45

Preparation of 13-(4-carboxylbenzyl)berberine chloride(comp. No. 45)

4-Carboxylbenzyl chloride, instead of 2-fluorobenzyl chloride of Example 8, was treated by the process described in Example 8 to give 4.17 g of 13-(4-carboxylbenzyl) berberine chloride. (Melting point: 153° C.)

EXAMPLE 46

Preparation of 13-(4-(2-hydroxy-2-propyl)benzyl) berberine choride(comp. No. 46)

4-(2-Hydroxy-2-propyl)benzyl) chloride, instead of 2-fluorobenzyl chloride of Example8, was treated by the process described i n Example 8 to give 4.97 g of 13-(4-(2-hydroxy-2-propyl)benzyl)berberine chloride. (Melting point: 105° C.)

EXAMPLE 47

Preparation of 13-(4-isopropoxvbenzyl)berberine chloride(comp. No. 47)

4-Isopropoxybenzyl chloride, instead of 2-fluorobenzyl chloride of Example 8, was treated by the process described in Example 8 to give 4.01 g of 13-(4-isopropoxybenzyl) berberine chloride. (Melting point: 127° C.)

EXAMPLE 48

Preparation of 13-(4-(2-butyl)benzyl)berberine chloride(comp. No. 48)

4-(2-Butyl)benzyl chloride, instead of 2-fluorobenzyl chloride of Example 8, was treated by the process described in Example 8 to give 3.77 g of 13-(4-(2-butyl)benzyl) berberine chloride. (Melting point: 106° C.)

EXAMPLE 49

Preparation of 13-(4-((2-methyl)-2-butyl)benzyl) berberine chloride(comp. No. 49)

4-((2-Methyl)-2-butyl)benzyl chloride, instead of 2-fluorobenzyl chloride of Example 8, was treated by the process described in Example 8 to give 3.15 g of 13-(4-((2-methyl)-2-butyl)benzyl)berberine chloride. (Melting point: 94° C.)

EXAMPLE 50

Preparation of 13-(4-pyrrolinylbenzyl)berberine chloride(comp. No. 50)

4-Pyrrolidinylbenzyl chloride, instead of 2-fluorobenzyl chloride of Example 8, was treated by the process described in Example 8 to give 3.15 g of 13-(4-pyrrolidinylbenzyl) berberine chloride. (Melting point: 108° C.)

EXAMPLE 51

Preparation of 13-(3-carboxylbenzylberberine chloride(comp. No. 51)

3-Carboxylbenzyl chloride, instead of 2-fluorobenzyl chloride of Example 8, was treated by the process described in Example 8 to give 3.56 g of 13-(3-carboxylbenzyl) berberine chloride. (Melting point: 136° C.)

EXAMPLE 52

Preparation of 13-(4-(3-pentoxy)benzyl)berberine chloride(comp. No. 52)

4-(3-Pentoxy)benzyl chloride, instead of 2-fluorobenzyl chloride of Example 8, was treated by the process described in Example 8 to give 3.77 g of 13-(4-(3-pentoxy)benzyl) berberine chloride. (Melting point: 135° C.)

EXAMPLE 53

Preparation of 13-(4-etoxycarbonyl)benzyl) berberine chloride(comp. No. 53)

4-(Etoxycarbonyl)benzyl chloride, instead of 2-fluorobenzyl chloride of Example 8, was treated by the process described in Example 8 to give 3.39 g of 13-(4-etoxycarbonylbenzyl)berberine chloride. (Melting point: 110° C.)

EXAMPLE 54

Preparation of 13-(4-methylthiobenzyl)berberine chloride(comp. No. 54)

4-Methylthiobenzyl chloride, instead of 2-fluorobenzyl chloride of Example 8, was treated by the process described in Example 8 to give 4.01 g of 13-(4-etbylthiobenzyl) berberine chloride. (Melting point: 106° C.)

EXAMPLE 55

Preparation of 13-(4-ethylthiobenzyl)berberine chloride(comp. No. 55)

4-Ethylthiobenzyl chloride, instead of 2-fluorobenzyl chloride of Example 8, was treated by the process described in Example 8 to give 3.81 g of 13-(4-ethylthio benzyl) berberine chloride. (Melting point: 142° C.)

EXAMPLE 56

Preparation of 13-(4-iodobenzyl)berberine chloride (comp. No. 56)

4-Iodobenzyl chloride, instead of 2-fluorobenzyl chloride of Example 8, was treated by the process described in Example 8 to give 4.01 g of 13-(4-iodobenzyl)berberine chloride. (Melting point: 167° C.)

EXAMPLE 57

Preparation of 13-(4-(1-hydroxy-2-propyl)benzyl) berberine chloride(comp. No. 57)

4-(1-Hydroxy-2-propyl)benzyl chloride, instead of 2-fluorobenzyl chloride of Example 8, was treated by the process described in Example 8 to give 2.98 g of 13-(4-(1-hydroxy-2-propyl)benzyl)berberine chloride. (Melting point: 112° C.)

EXAMPLE 58

Preparation of 13-(3-phenoxybenzyl)berberine chloride(comp. No. 58)

3-Phenoxybenzyl chloride, instead of 2-fluorobenzyl chloride of Example 8, was treated by the process described in Example 8 to give 3.98 g of 13-(3-phenoxybenzyl) berberine chloride. (Melting point: 231° C.)

NMR(300 MHz, CDCl$_3$) δ: 3.30–3.34(broad t, J=5.7 Hz, 2H), 4.05(s, 3H), 4.40(s, 3H), 4.66(s, 2H), 5.18–5.22(broad t, J=5.7 Hz, 2H), 6.06(s, 2H), 6.81–7.01(m, 7H), 7.09–7.14 (broad t, J=6.0 Hz, 1H), 7.30–7.35(m, 3H), 7.63–7.66(d, J=9.0 Hz, 1H), 7.72–7.75(d, J=9.0 Hz, 1H), 10.43(s, 1H)

EXAMPLE 59

Preparation of 13-(4-benzyloxvbenzyl)berberine chloride(comp. No. 59)

4-Benzyloxbenzyl chloride, instead of 2-fluorobenzyl chloride of Example 8, was treated by the process described in Example 8 to give 4.05 g of 13-(4-benzyloxybenzyl) berberine chloride. (Melting point: 176–178° C.)

NMR(300 MHz, CDCl$_3$) δ: 3.28–3.32(broad t, J=6.0 Hz, 2H), 4.05(s, 3H), 4.37(s, 3H), 4.69(s, 2H), 5.05(s, 2H), 5.06–5.10(broad t, J=6.0 Hz, 2H), 6.03(s, 2H), 6.89(s, 1H), 6.80–7.43(m, 10H), 7.67–7.70(d,J=9.3 Hz, 1H), 7.72–7.75 (d, J=9.3 Hz, 1H), 10.18(s, 1H)

EXAMPLE 60

Preparation of 13-(4-vinylbenzyl)berberine chloride (comp. No. 60)

4-Vinylbenzyl chloride, instead of 2-fluorobenzyl chloride of Example 8, was treated by the process described in Example 8 to give 3.81 g of 13-(4-vinylbenzyl) berberine chloride. (Melting point: 144° C.)

NMR(300 MHz, CDCl$_3$) δ: 3.1–3.35(broad t, J=5.7 Hz, 2H), 4.02(s, 3H), 4.42(s, 3H), 4.66(s, 2H), 5.17–5.21(broad t, J=5.7 Hz, 2H), 5.25–5.30(dd, J=3.0, 10.8 Hz, 1H), 5.70–5.79(dd, J=10.8, 17.1 Hz, 1H), 6.01(s, 2H), 6.88(s, 1H), 6.96(s, 1H), 7.08–7.10(d, J=8.1 Hz, 2H), 7.40–7.43(d, J=8.1 Hz, 2H), 7.58–7.72(m, 3H), 10.42(s, 1H)

EXAMPLE 61

Preparation of 13-(4-methoxycarbonylbenzyl) berberine chloride(comp. No. 61)

4-Methoxycarbonylbenzyl chloride, instead of 2-fluorobenzyl chloride of Example 8, was treated by the process described in Example 8 to give 3.81 g of 13-(4-methoxycarbonylbenzyl)berberine chloride. (Melting point: 198° C.)

NMR(300 MHz, CDCl$_3$) δ: 3.27–3.31(broad t, J=5.7 Hz, 2H), 3.92(s, 3H), 4.04(s, 3H), 4.37(s, 3H), 4.97(s, 2H), 5.16–5.20(broad t,J=5.7 Hz, 2H), 6.01(s, 2H), 6.86(s, 1H), 6.90(s, 1H), 7.23–7.26(d, J=8.1 Hz, 2H), 7.56–7.60(d, J=9.3 Hz, 1H), 7.71–7.74(d, J=9.3 Hz, 1H), 8.04–8.07(d, J=8.1 Hz, 2H), 10.34(s, 1H)

EXAMPLE 62

Preparation of 13-(4-t-butylbenzyl)berberine chloride(comp. No. 62)

4-t-Butylbenzyl chloride, instead of 4-chlorobenzyl chloride of Example 2, was treated by the process described in Example 2 to give 2.3 g of 13-(4-t-butylbenzyl)berberine choride, or 4-t-butylbenzyl chloride, instead of 2-fluorobenzyl chloride of Example 8, was treated by the process described in Example 8 to give 3.81 g of 13-(4-t-butylbenzyl)berberine chloride. (Melting point: 144° C.)

NMR(300 MHz, DMSO-d$_6$) δ: 1.26(s, 9H), 3.21(t, 2H), 4.09(s, 3H), 4.17(s, 3H), 4.80(s, 2H), 4.91(broad t, 2H), 6.17(s, 2H), 6.99(s, iH), 7.11(d, 2H), 7.16(s, 1H), 7.38(d, 2H), 7.78(d, 1H), 8.10(d, 1H), 10.05(s, 1H)

EXAMPLE 63

Preparation of 13-(4-i-propylbenzyl)berberine chloride(comp. No. 63)

4-i-propylbenzyl chloride, instead of 4-chlorobenzyl chloride of Example 2, was treated by the process described in Example 2 to give 2.3 g of 13-(4-i-propylbenzyl) berberine chloride, or 4-benzyl chloride, instead of 2-fluorobenzyl chloride of Example 8, was treated by the process described in Example 8 to give 3.40 g of 13-(4-i-propylbenzyl)berberine chloride. (Melting point: 142° C.)

NMR(300 MHz, DMSO-d$_6$) δ: 1.41(d, 6H), 3.18(t, 2H), 3.40(q, 1H), 4.10(s, 3H), 4.16(s, 3H), 4.820(s, 2H), 4.90 (broad t, 2H), 6.21(s, 2H), 6.88(s, 1H), 7.12(d, 2H), 7.16(s, 1H), 7.40(d, 2H), 7.75(d, 1H), 8.09(d, 1H), 10.05(s, 1H)

EXAMPLE 64

Preparation of 8-hydroxy-13-(4t-butylbenzyl) berberine chloride(comp. No. 64)

To a suspension of 1.0 g(2 mmol) of the compound No. 62 in 10 ml of distilled water was added dropwise 0.23 g of 30% aqueous of hydrogen peroxide and 0.18 g of 45% NaOH aqueous solution, consecutively and then reacted at room temperature for 1 hour. The solid so precipitated was filtered and dried to give 0.75 g of 8-hydroxy-13-(4-t-butylbenzyl)berberine chloride.

NMR(300 MHz, CDCl$_3$) δ: 1.32(s, 9H), 3.29–3.33(broad t, J=5.7 Hz, 2H), 4.06(s, 3H), 4.37(s, 3H), 4.73(s, 2H), 4.97–5.01(broad t, J=5.7 Hz, 2H), 6.03(s, 2H), 6.90(s, 1H), 7.06(s, 1H), 7.06–7.08(d, J=8.1 Hz, 2H), 7.35–7.38(d, J=8.1 Hz, 2H), 7.70–7.73(d,J=9.0 Hz, 1H), 7.75–7.78(d,J=9.0 Hz, 1H), 9.91(s, 1H)

EXAMPLE 65

Preparation of 13-(2-picolyl)berberine chloride (comp. No. 65)

2-Picolyl chloride, instead of 2-fluorobenzyl chloride of Example 8, was treated by the process described in Example 8 to give 3.81 g of 13-(2-picolyl) berberine chloride. (Melting point: 122–124° C.)

NMR(300 MHz, CDCl$_3$) δ: 3.30–3.34(broad t, J=5.7 Hz, 2H), 4.00(s, 3H), 4.36(s, 3H), 4.86(s, 2H), 5.12–5.16(broad t,J=5.7 Hz, 2H), 6.02(s, 2H), 6.89(s, 1H), 7.24–7.26(m, 1H), 7.35(s, 1H), 7.45–7.48(d, J=7.8 Hz, 1H), 7.55–7.58(d, J=9.6 Hz, 1H), 7.67–7.71(d, J=9.6 Hz, 1H), 7.76–7.83(m, 1H), 8.50–8.52(d, J=3.6 Hz, 1H), 10.27(s, 1H)

EXAMPLE 66

Preparation of 13-benzyl palmatine iodide(comp. No. 66)

A mixture 10 g of palmatine hydrochloride, 40 ml of water, 15 ml of 50% NaOH aqueous solution was stirred vigorously for 30 minutes. The reaction mixture was filtered. The solid thus obtained was washed twice with 20 ml of methanol and dried to obtain 7.0 g of 8-acetonyl dihydropalmatine. To a solution of 5 g of 8-acetonyldihydropalmatine in 30 ml of acetonitrile was added 15 ml of benzyl chloride and 10 g of sodium iodide and then the mixture was heated to reflux for 3 hours. The reaction mixture was concentrated and purified by chromatography over silica gel eluting with methanol/dichloromethane (1:75) to give 3.0 g of 13-benzylpalmatine iodide.

NMR(300 MHz, DMSO-d$_6$) δ: 3.25(t, 2H), 3.80(s, 3H), 4.03(s, 3H), 4.12(s, 3H), 4.13(s, 3H), 4.80(s, 2H), 4.91(t, 2H), 6.90(s, 1H), 7.01(m, 2H), 7.10(s, 1H), 7.17(m, 3H), 7.86(d, 1H), 8.17(d, 1H), 10.11(s, 1H)

EXAMPLE 67

Preparation of 13-(4-chlorobenzyl)palmatine iodide (comp. No. 67)

A mixture of 5 g of 8-acetonyldihydropalmatine was dissolved in 30 ml of acetonitrile, and 15 ml of benzyl chloride and 10 g of sodium iodide were added thereto and then, refluxed for 3 hours. The reaction mixture was concentrated and adsorbed with Celite, and then liquid-chromatographed over 60 g of silica gel and eluted with methanol/dichloromethane (1:75) to obtain 2.7 g of 13-(4-chloro benzyl)palmatine iodide.

NMR(300 MHz, DMSO-d$_6$) δ: 3.21(t, 2H), 3.81(s, 3H), 4.02(s, 3H), 4.13(s, 3H), 4.14(s, 3H), 4.80(s, 2H), 4.91 (broad t, 2H), 6.90(s, 1H), 7.05(d, 2H), 7.17(s, 1H), 7.42(d, 2H), 7.86(d, 1H), 8.17(d, 1H), 10.10(s, 1H)

EXAMPLE 68

Preparation of 13-(3-chlorobenzyl)palmatine iodide (comp. No. 68)

3-Chlorobenzyl chloride, instead of 4-chlorobenzyl chloride of Example 67, was treated by the process described in Example 68 to give 2.8 g of 13-(3-chlorobenzyl)palmatine iodide.

NMR(300 MHz, DMSO-d$_6$) δ: 3.20(t, 2H), 3.81(s, 3H), 4.00(s, 3H), 4.11(s, 3H), 4.12(s, 3H), 4.70(s, 2H), 4.85 (broad t, 2H), 6.90(s, 1H), 7.12(s, 1H), 7.17(s, 1H), 7.30(t, 1H), 7.40(d, 1H), 7.76(d, 1H), 8.10(d, 1H), 10.15(s, 1H)

EXAMPLE 69

Preparation of 13-(2-chlorobenzyl) palmatine iodide (comp. No. 69)

2-Chlorobenzyl chloride, instead of 4-chlorobenzyl chloride of Example 67, was treated by the process described in Example 67 to give 2.3 g of 13-(2-chlorobenzyl)palmatine iodide.

NMR(300 MHz, DMSO-d$_6$) δ: 3.20(t, 2H), 3.81(s, 3H), 4.03(s, 3H), 4.12(s, 6H), 4.65(s, 2H), 4.91(broad t, 2H), 6.74(s, 1H), 6.80(d, 2H), 7.17(s, 1H), 7.24(t, 1H), 7.34(t, 1H), 7.68(d, 1H), 7.70(d, 1H), 8.11(d, 1H), 10.15(s, 1H)

EXAMPLE 70

Preparation of 13-(4-bromobenzyl) palmatine iodide (comp. No. 70)

4-Bromobenzyl chloride, instead of 4-chlorobenzyl chloride of Example 67, was treated by the process described in Example 67 to give 2.5 g. of 13-(4-bromobenzyl)palmatine iodide.

NMR(300 MHz, DMSO-d$_6$) δ: 3.21(t, 2H), 3.80(s, 3H), 4.02(s, 3H), 4.13(s, 3H), 4.14(s, 3H), 4.80(s, 2H), 4.91 (broad t, 2H), 6.91(s, 1H), 7.13(d, 2H), 7.16(s, 1H), 7.55(d, 2H), 7.70(d, 1H), 8.11(d, 1H), 10.05(s, 1H)

EXAMPLE 71

Preparation of 13-(3-bromobenzyl)palmatine iodide (comp. No. 71)

3-Bromobenzyl chloride, instead of 4-chlorobenzyl chloride of Example 67, was treated by the process described in Example 67 to give 2.8 g of 13-(3-bromobenzyl)palmatine iodide.

NMR(300 MHz, DMSO-d$_6$) δ: 3.20(t, 2H), 3.80(s, 3H), 4.03(s, 3H), 4.14(s, 6H), 4.70(s, 2H), 4.85(broad t, 2H), 6.91(s, 1H), 7.15(s, 1H), 7.17(s, 1H), 7.31(t, 1H), 7.48(d, 1H), 7.50(d, 1H), 7.76(d, 1H), 8.09(d, 1H), 10.02(s, 1H)

EXAMPLE 72

Preparation of 13-(4-methylbenzyl)palmatine iodide (comp. No. 72)

4-Methylbenzyl chloride, instead of 4-chlorobenzyl chloride of Example 67, was treated by the process described in Example 67 to give 2.2 g of 13-(4-methylbenzyl)palmatine iodide.

NMR(300 MHz, DMSO-$d_6$) δ: 2.23(s, 3H), 3.21(t, 2H), 3.80(s, 3H), 4.02(s, 3H), 4.13(s, 3H), 4.14(s, 3H), 4.60(s, 2H), 4.82(broad t, 2H), 6.97(s, 1H), 7.06(d, 2H), 7.16(s, 1H), 7.17(d, 2H), 7.82(d, 1H), 8.05(d, 1H), 10.05(s, 1H)

EXAMPLE 73

Preparation of 13-(3-methylbenzyl)palmatine iodide (comp. No. 73)

3-Methylbenzyl chloride, instead of 4-chlorobenzyl chloride of Example 67, was treated by the process described in Example 67 to give 2.1 g of 13-(3-methylbenzyl)palmatine iodide.

NMR(300 MHz, DMSO-$d_6$) δ: 2.27(s, 3H), 3.20(t, 2H), 3.86(s, 3H), 4.02(s, 3H), 4.11(s, 3H), 4.14(s, 3H), 4.70(s, 2H), 4.95(broad t, 2H), 6.92(d, 1H), 7.00(s, 1H), 7.07(d, 1H), 7.11(d, 1H), 7.18(s, 1H), 7.24(t, 1H), 7.82(d, 1H), 7.76(d, 1H), 8.11(d, 1H), 10.05(s, 1H)

EXAMPLE 74

Preparation of 13-(2-methylbenzyl)palmatine iodide (comp. No. 74)

2-Methylbenzyl chloride, instead of 4-chlorobenzyl chloride of Example 67, was treated by the process described in Example 67 to give 2.5 g of 13-(2-methylbenzyl)palmatine iodide.

NMR(300 MHz, DMSO-$d_6$) δ: 2.25(s, 3H), 3.18(t, 2H), 3.85(s, 3H), 4.00(s, 3H), 4.11(s, 3H), 4.13(s, 3H), 4.55(s, 2H), 4.95(broad t, 2H), 6.61(d, 1H), 6.79(s, 2H), 7.06(t, 1H), 7.16(s, 1H), 7.22(t, 1H), 7.40(d, 1H), 7.72(d, 1H), 8.11(d, 1H), 10.05(s, 1H)

EXAMPLE 75

Preparation of 13-(3,4-dimethylbenzyl) palmatine iodide(comp. No. 75)

3,4-Dimethylbenzyl chloride, instead of 4-chlorobenzyl chloride of Example 67, was treated by the process described in Example 67 to give 2.7 g of 13-(3,4-dimethylbenzyl)palmatine iodide.

NMR(300 MHz, DMSO-$d_6$) δ: 2.18(s, 3H), 2.20(s, 3H), 3.21(t, 2H), 3.79(s, 3H), 4.02(s, 3H), 4.11(s, 3H), 4.13(s, 3H), 4.65(s, 2H), 4.91(broad t, 2H), 6.81(d, 1H), 7.01(s, 1H), 7.03(d, 1H), 7.10(s, 1H), 7.17(s, 1H), 7.70(d, 1H), 8.10(d, 1H), 10.05(s, 1H)

EXAMPLE 76

Preparation of 13-(2,4-dimethylbenzyl)palmatine iodide(comp. No. 76)

2,4-Dimethylbenzyl chloride, instead of 4-chlorobenzyl chloride of Example 67, was treated by the process described in Example 67 to give 2.4 g of 13-(2,4-dimethylbenzyl)palmatine iodide.

NMR(300 MHz, DMSO-$d_6$) δ: 2.27(s, 3H), 2.42(s, 3H), 3.20(t, 2H), 3.78(s, 3H), 4.00(s, 3H), 4.09(s, 3H), 4.11(s, 3H), 4.50(s, 2H), 4.90(broad t, 2H), 6.50(d, 1H), 6.80(s, 1H), 6.88(dd, 1H), 7.16(s, 1H), 7.21(d, 1H), 7.67(d, 1H), 8.10(d, 1H), 10.05(s, 1H)

EXAMPLE 77

Preparation of 13-(4-t-butylbenzyl)palmatine iodide (comp. No. 77)

4-t-Butylbenzyl chloride, instead of 4-chlorobenzyl chloride of Example 67, was treated by the process described in Example 67 to give 2.9 g of 13-(4-t-butylbenzyl)palmatine iodide.

NMR(300 MHz, DMSO-$d_6$) δ: 1.26(s, 9H), 3.21(t, 2H), 3.80(s, 3H), 4.00(s, 3H), 4.13(s, 3H), 4.14(s, 3H), 4.91 (broad t, 2H), 6.99(s, 1H), 7.11(d, 2H), 7.16(s, 1H), 7.38(d, 2H), 7.78(d, 1H), 8.10(d, 1H), 10.05(s, 1H)

EXAMPLE 78

Preparation of 13-(4-(N,N-dimethylamino)benzyl) palmatine iodide(comp. No. 78)

4-(N,N-dimethylamino)benzyl chloride, instead of 4-chlorobenzyl chloride of Example 67, was treated by the process described in Example 67 to give 2.8 g of 13-(4-(N,N-dimethylamino)benzyl)palmatine iodide. (Melting point: 149° C.)

EXAMPLE 79

Preparation of N'-methylammonium iodide of 13-(4-(N,N-dimethyl amino)benzyl)palmatine iodide (comp. No. 79)

4-Chloromethylphenyltrimethylammonium iodide, instead of 4-chlorobenzyl chloride of Example 67, was treated by the process described in Example 67 to give 2.7 g of N'-methylammonium iodide of 13-(4-(N,N-dimethylamino)benzyl) palmatine iodide. (Melting point: 151° C.)

EXAMPLE 80

Preparation of N'-ethylammonium iodide of 13-(4-(N,N-dimethyl amino)benzyl)palmatine iodide (comp. No. 80)

(4-Chloromethylphenyl)dimethyethyllammonium iodide, instead of 4-chlorobenzyl chloride of Example 67, was treated by the process described in Example 67 to give 3.0 g of N'-ethylammonium iodide of 13-(4-(N,N-dimethylamino)benzyl)palmatine iodide. (Melting point: 153° C.)

EXAMPLE 81

Preparation of 13-(2-fluoro-4-t-butylbenzyl) palmatine iodide(comp. No. 81)

2-Fluoro-4-t-butylbenzyl chloride, instead of 4-chlorobenzyl chloride of Example 67, was treated by the process described in Example 67 to give 2.7 g of 1 3-(2-fluoro-4-t-butylbenzyl)palmatine iodide. (Melting point: 157° C.)

EXAMPLE 82

Preparation of 13-(4-(2-hydroxy-2-propyl)benzyl) palmatine iodide(comp. No. 82)

4-(2-Hydroxy-2-propyl)benzyl chloride, instead of 4-chlorobenzyl chloride of Example 67, was treated by the process described in Example 67 to give 2.6 g of 13-(4-(2-hydroxy-2-propyl)benzyl)palmatine iodide. (Melting point: 112° C.)

EXAMPLE 83

Preparation of 13-(4-(2-methyl-2-butyl)benzyl) palmatine iodide(comp. No. 83)

4-(2-Methyl-2-butyl)benzyl chloride, instead of 4-chlorobenzyl chloride of Example 67, was treated by the process described in Example 67 to give 2.3 g of 13-(4-(2-methyl-2-butyl)benzyl)palmatine iodide. (Melting point: 110° C.)

EXAMPLE 84

Preparation of 13-(4-methylthiobenzyl)palmatine iodide(comp. No. 84)

4-Methylthiobenzyl chloride, instead of 4-chlorobenzyl chloride of Example 67, was treated by the process described in Example 67 to give 2.7 g of 13-(4-methylthiobenzyl)palmatine iodide. (Melting point: 110° C.)

EXAMPLE 85

Preparation of 2,3,9,10-tetrapropoxy protoberberine iodide (comp. No. 85)

Berberine hydrochloride (2.5 g) was reacted with 12.5 g of anhydrous aluminum chloride with stirring at 150° C. for 1 hour, and 250 ml of 5% dilute hydrochloric acid was added to the reaction mixture. The mixture was heated to dissolve thoroughly and then cooled to 4° C. to precipitate a solid product. The solid thus obtained was filtered off and recrystallized from methanol to obtain 1.5 g of 2,3.9,10-tetrahydroxy protoberberine. To a solution of 5.0 g of 2,3,9,10-tetrahydroxy protoberberine in 200 ml of acetonitrile was added 12.5 g of potassium carbonate. The mixture was heated and 11.7 ml of n-propyl iodide was added thereto dropwise under reflux for 5 hours. The reaction mixture was concentrated and then adsorbed with Celite and liquid-chromatographed over 60 g of silica gel and eluted with methanol/dichloromethane(1:25) to obtain 2.87 g of 2,3,9,10-tetrapropoxyprotoberberine iodide.

NMR(300 MHz, DMSO-$d_6$) δ: 1.10(m, 12H), 1.90(m, 6H), 2.00(m, 2H), 3.30(t, 2H), 4.10(m, 6H), 4.47(t, 2H), 5.15(t, 2H), 6.74(s, 1H), 7.41(d, 2H), 7.70(d, 2H), 7.98(d, 1H), 8.52(s, 1H), 9.92(s, 1H)

EXAMPLE 86

Preparation of 13-(4-t-butylbenzyl)berberine sulphate(comp. No. 86)

To a solution of 5 g of 13-(4-t-butylbenzyl)berberine chloride(compound No. 62) in 25 ml of acetone was added dropwise 5 g of 45% aqueous NaOH solution. The reaction mixtures stirred at room temperature and 20 ml of distilled water was added thereto every two hours and after 5 hours, 30 ml of distilled water was added thereto. The solid thus precipitated was filtered to obtain 5.1 g of 8-acetonyl-13-(4-t-butylbenzyl)berberine. To 1g of 8-acetonyl-13-(4-t-butylbenzyl) berberine was added 4 ml of 1.0 M $H_2SO_4$. The reaction was proceeded at room temperature for 2 hours. The solid thus obtained is filtered and washed with small amount of distilled water and dried to obtain 0.8 g of 13-(4-t-butylbenzyl)berberine sulphate. (Melting point: 152° C.)

EXAMPLE 87

Preparation of 13-(4-t-butylbenzyl)berberine acetate (comp. No. 87)

Acetic acid (3 ml), instead of 1.0 M $H_2SO_4$ of Example 86, was treated by the process described in Example 86 to give 0.5 g of 13-(4-t-butylbenzyl)berberine acetate. (Melting point: 171° C.)

EXAMPLE 88

Preparation of 13-(4-t-butylbenzyl)palmatine nitrate (comp. No. 88)

13-(4-t-Butylbenzyl) palmatine iodide obtained in Example 77, instead of 13-(4-t-butylbenzyl)berberine chloride of Example 86, was treated by the process described in Example 86 to obtain 8-acetonyl-13-(4-t-butylbenzyl) palmatine. Then, 1.3 M $HNO_3$, instead of 1.0 M $H_2SO_4$ of Example 57, was employed to obtain 0.8 g of 13-(4-t-butylbenzyl)palmatine nitrate. (Melting point: 146° C.)

EXAMPLE 89

Preparation of 13-benzyldihydroberberine (comp. No. 89)

To a vigorously stirred solution of 13-benzyl berberine iodide obtained in Example 1 in 50 ml of THF was added 5 ml of 1.0 M $LiAlH_4$ in a stream. After the reaction mixture was stirred for 1 hour, the reaction mixture was concentrated under vacuo and then extracted twice with 20 ml of dichloromethane. The organic extract was concentrated and then recrystallized from methanol to obtain 1.7 g of 13-benzyldihydroberberine.

NMR(300 MHz, $CDCl_3$) δ: 2.60(m, 2H), 3.20(m, 2H), 3.66(d, 1H), 3.85(s, 2H), 3.87(s, 3H), 3.95(s, 3H), 4.27(d, 1H), 5.99(s, 2H), 6.03(d, 1H), 6.57(d, 1H), 6.65(s, 1H), 6.75(s, 1H), 6.83–7.06(m, 5H)

EXAMPLE 90

Preparation of 13-(4-chlorobenzyl)dihydroberberine (comp. No. 90)

13-(4-Chlorobenzyl)berberine iodide(2.0 g)obtained in Example 2, instead of 13-benzylberberine iodide of Example 89, is treated by the process described in Example 89 to obtain 1.67 g of 13-(4-chlorobenzyl)dihydroberberine.

NMR(300 MHz, $CDCl_3$) δ: 2.50(m, 2H), 3.21(m, 2H), 3.66(d, 1H), 3.86(s, 2H), 3.88(s, 3H), 3.99(s, 3H), 4.27(d, 1H), 5.99(s, 2H), 6.05(d, 1H), 6.63(d, 1H), 6.70(s, 1H), 6.75(d, 2H), 6.80(s, 1H), 7.14(d, 2H)

EXAMPLE 91

Preparation of 13-(3-chlorobenzyl)dihydroberberine (comp. No. 91)

13-(3-Chlorobenzyl)berberine iodide(2.0 g) obtained in Example 3, instead of 13-benzylberberine iodide of Example 89, is treated by the process described in Example 89 to obtain 1.61 g of 13-(3-chlorobenzyl)dihydroberberine.

NMR(300 MHz, $CDCl_3$) δ: 2.80–3.20(m, 4H), 3.60(d, 1H), 3.75(s, 2H), 3.83(s, 3H), 3.88(s, 3H), 4.17(d, 1H), 6.07(s, 2H), 6.13(d, 1H), 6.60(d, 1H), 6.65(s, 1H), 7.05–7.15 (m, 4H), 7.15(s, 1H)

EXAMPLE 92

Preparation of 13-(2-chlorobenzyl)dihydroberberine (comp. No. 92)

13-(2-Chlorobenzyl)berberine iodide(2.0 g) obtained in Example 2, instead of 13-benzylberberine iodide of Example 89, is treated by the process described in Example 89 to obtain 1.50 g of 13-(2-chlorobenzyl)dihydroberberine.

NMR(300 MHz, $CDCl_3$) δ: 2.80(m, 2H), 3.16(m, 2H), 3.57(d, 1H), 3.73(s, 3H), 3.75(s, 2H), 3.83(s, 3H), 4.15(d, 1H), 6.07(s, 2H), 6.14(d, 1H), 6.70(d, 1H), 6.73(s, 1H), 6.86(d, 1H), 7.01(t, 1H), 7.10(t, 1H), 7.12(s, 1H), 7.21(d, 1H)

EXAMPLE 93

Preparation of 13-(4-bromobenzyl)dihydroberberine (comp. No. 93)

13-(4-Bromobenzyl)berberine iodide(2.0 g) obtained in Example 5, instead of 13-benzylberberine iodide of Example 89, is treated by the process described in Example 89 to obtain 1.61 g of 13-(4-bromobenzyl)dihydroberberine.

NMR(300 MHz, CDCl$_3$) δ: 2.50(m, 2H), 3.21(m, 2H), 3.66(d, 1H), 3.86(s, 2H), 3.88(s, 2H), 3.99(s, 3H), 4.27(d, 1H), 5.99(s, 21H), 6.05(d, 1H), 6.63(d, 1H), 6.70(s, 1H), 6.75(d, 2H), 6.80(d, 2H), 7.14(d, 2H)

EXAMPLE 94

Preparation of 13-(3-bromobenzyl)dihydroberberine (comp. No. 94)

13-(3-Bromobenzyl)berberine iodide(2.0 g)obtained in Example 6, instead of 13-benzylberberine iodide of Example 89, is treated by the process described in Example 89 to obtain 1.57 g of 13-(3-bromobenzyl)dihydroberberine.

NMR(300 MHz, CDCl$_3$) δ: 2.70(m, 2H), 3.20(m, 2H), 3.65(d, 1H), 3.70(s, 2H), 3.78(s, 2H), 3.80(s, 3H), 4.10(d, 1H), 6.02(s, 2H), 6.13(d, 1H), 6.62(d, 1H), 6.70(s, 1H), 6.90–7.05(m, 4H), 7.12(s, 1H)

EXAMPLE 95

Preparation of 13-(4-methylbenzyl)dihydroberberine (comp. No. 95)

13-(4-Methylbenzyl)berberine chloride(2.0 g) obtained in Example 15, instead of 13-benzylberberine iodide of Example 89, is treated by the process described in Example 89 to obtain 1.43 g of 13-(4-methylbenzyl)dihydroberberine.

NMR(300 MHz, CDCl$_3$) δ: 2.26(s ,3H), 2.57(m, 2H), 3.18(m, 2H), 3.66(d, 1H), 3.77(s, 2H), 3.80(s, 3H), 3.89(s, 3H), 4.12(d, 1H), 5.97(s, 2H), 6.21(d, 1H), 6.67(d, 1H), 6.71(s, 1H), 6.75(d, 2H), 6.82(s, 1H), 7.21(d, 2H)

EXAMPLE 96

Preparation of 13-(3-methylbenzyl)dihydroberberine (comp. No. 96)

13-(3-Methylbenzyl)berberine chloride(2.0 g) obtained in Example 16, instead of 13-benzylberberine iodide of Example 89, is treated by the process described in Example 89 to obtain 1.61 g of 13-(3-methylbenzyl)dihydroberberine.

NMR(300 MHz, CDCl$_3$) δ:-2.20(s ,3H), 2.80–3.20(m, 4H), 3.66(d, 1H), 3.75(s, 2H), 3.83(s, 3H), 3.88(s, 3H), 4.17(d, 1H), 6.07(s, 2H), 6.13(d, 1H), 6.60(d, 1H), 6.65(s, 1H), 7.05–7.15(m, 4H), 7.15(s, 1H)

EXAMPLE 97

Preparation of 13-(2-methylbenzyl)dihydroberberine (comp. No. 97)

13-(2- Methylbenzyl)berberine chloride(2.0 g)obtained in Example 17, instead of 13-benzylberberine iodide of Example 89, is treated by the process described in Example 89 to obtain 1.67 g of 13-(2-methylbenzyl)dihydroberberine.

NMR(300 MHz, CDCl$_3$) δ: 2.27(s ,3H), 2.78(m, 2H), 3.17(m, 2H), 3.59(d, 1H), 3.75(s, 2H), 3.78(s, 3H), 3.83(s, 3H), 4.16(d, 1H), 6.01(s, 2H), 6.24(d, 1H), 6.71(d, 1H), 6.73(s, 1H), 6.87(d, 1H), 7.02(t, 1H), 7.08(t, 1H), 7.11(s, 1H), 7.19(d, 1H)

EXAMPLE 98

Preparation of 13-(3,4-dimethylbenzyl) dihydroberberine(comp. No. 98)

13-(3,4-Dimethylbenzyl)berberine chloride(2.0 g) obtained in Example 18, instead of 13-benzylberberine iodide of Example 89, is treated by the process described in Example 89 to obtain 1.53 g of 13-(3,4-dimethylbenzyl) dihydroberberine.

NMR(300 MHz, CDCl$_3$) δ: 2.21(s, 3H), 2.25(s ,3H), 2.59(m, 2H), 3.10(m, 2H), 3.67(d, 1H), 3.80(s, 2H), 3.85(s, 3H), 3.91(s, 3H), 4.15(d, 1H), 5.99(s, 2H), 6.25(d, 1H), 6.69(d, 1H), 6.73(s, 1H), 6.80(d, 1H), 7.01(d, 1H), 7.22(d, 1H), 7.27(s, 1H)

EXAMPLE 99

Preparation of 13-(2,4-dimethylbenzyl) dihydroberberine(comp. No. 99)

13-(2,4-Dimethylbenzyl)berberine chloride (2.0 g) obtained in Example 19, instead of 13-benzylberberine iodide of Example 89, is treated by the process described in Example 89 to obtain 1.47 g of 13-(2,4-dimethylbenzyl) dihydroberberine.

NMR(300 MHz, CDCl$_3$) δ: 2.25(s, 3H), 2.26(s ,3H), 2.60(m, 2H), 3.20(m, 2H), 3.65(d, 1H), 3.79(s, 2H), 3.82(s, 3H), 3.89(s, 3H), 4.21(d, 1H), 6.01(s, 2H), 6.17(d, 1H), 6.75(d, 1H), 6.82(d, 1H), 6.02(d, 1H), 7.10(d, 1H), 7.14(s, 1H), 7.25(d, 1H)

EXAMPLE 100

Preparation of 13-(4-t-butylbenzyl)dihydroberberine (comp. No. 100)

To a solution of 4-t-butylbenzyl chloride (1.20 g, 6.6 mmol) in 50 ml of acetonitrile was added 0.998(6.6 mmol) of NaI. After the reaction was proceeded at room temperature for 1 hour, 2.02 g(6.0 mmol) of 8-hydroberberine was added to the reaction mixture. The reaction mixture was refluxed under N$_2$ atmosphere for 5 hours. The resulting mixture was concentrated and then dissolved in 100 ml of chloroform and quenched with 10% aqueous solution of K$_2$CO$_3$ The organic layer was separated and dried over MgSO$_4$ and filtered. The filtrate was concentrated. The resulting solid was triturated in 20 ml of diethylether and filtered to obtain 2.60 g of 13-(4-t-butylbenzyl) dihydroberberine NMR(300 MHz, CDCl$_3$) δ: 1.31(s, 9H), 2.80–2.84(broad t, J=5.7 Hz, 2H), 3.15–3.19(broad t,J=5.7 Hz, 2H), 3.81(s, 3H), 3.86(s, 3H), 4.10(s, 2H), 4.40(s, 2H), 5.89(s, 2H), 6.65(s, 1H), 6.65–6.68(d, J=8.4 Hz, 1H), 6.78–6.81(d, J=8.4 Hz, 1H), 6.93(s, 1H), 7.22–7.25(d,J=8.1 Hz, 2H), 7.30–7.32 (d,J=8.1 Hz, 2H)

EXAMPLE 101

Preparation of 13-(4-picolyl)dihydroberberine (comp. No. 101)

4-Picolylchloride(0.84 g), instead of 4-t-butylbenzyl chloride of Example 100, is treated by the process described in Example 100 to obtain 2.01 g of 13-(4-picolyl) dihydroberberine.

NMR(300 MHz, DMSO-d$_6$) δ: 2.73–2.77(broad t, J=5.7 Hz, 2H), 3.07–3.11(broad t,J=5.7 Hz, 2H), 3.72(s,3H),3.73 (s, 3H), 4.04(s, 2H), 4.34(s, 2H), 5.95(s, 2H), 6.56–6.58(d, J=8.1 Hz, 1H), 6.58(s, 1H), 6.74–6.76(d, J=8.1 Hz, 1H), 6.88(s, 1H), 7.28–7.29(d, J=5.4 Hz, 2H), 8.46–8.48(d, J=5.4 Hz, 2H)

EXAMPLE 102

Preparation of 13-(2-hydroxy-5-nitrobenzyl) dihydroberberine(comp. No. 102)

2-Hydroxy-5-nitrobenzylbromide(1.53 g), instead of 4-t-butyl benzyl chloride of Example 100, is treated by the process described in Example 100 to obtain 2.60 g of 13-(2-hydroxy-5-nitrobenzyl)dihydroberberine.

NMR(300 MHz, DMSO-d$_6$) δ: 3.09–3.13(m, 4H), 3.34–3.38 (broad t, J=5.7 Hz, 2H), 3.79(s, 3H), 3.83(s, 3H), 5.06(s, 2H), 6.14(s, 1H), 6.23(s, 1H), 6.84–6.87(d, J=8.7 Hz, 1H), 6.99–7.02(d, J=8.4 Hz, 1H), 7.07(s, 1H), 7.15–7.18(d, J=8.4 Hz, 1H), 7.61–7.62(d, J=2.4 Hz, 1H), 7.71(s, 1H), 7.93–7.96(dd, J=2.4, 8.7 Hz, 1H), 11.38(s, 1H)

EXAMPLE 103

Preparation of 13-benzyldihydropalmatine (comp. No. 103)

13-Benzyl palmatine iodide (2.0 g) obtained in Example 66, instead of 13-benzyl berberine iodide of Example 89, is treated by the process described in Example 89 to obtain 1.75 g of 13-benzyldihydropalmatine.

NMR(300 MHz, CDCl$_3$) δ: 2.60(m, 2H), 3.22(m, 2H), 3.67(d, 1H), 3.87(s, 2H), 3.88(s, 3H), 3.94(s, 3H), 3.95(s, 3H), 3.96(s, 3H), 4.27(d, 1H), 6.05(d, 1H), 6.63(d, 1H), 6.70(s, 1H), 6.87(m, 3H), 6.92(m, 2H), 7.16(s, 1H)

EXAMPLE 104

Preparation of 13-(4-chlorobenzyl)dihydropalmatine (comp. No. 104)

13-(4-Chlorobenzyl)palmatine iodide(2.0 g) obtained in Example 67, instead of 13-benzyl berberine iodide of Example 89, is treated by the process described in Example 89 to obtain 1.61 g of 13-(4-chlorobenzyl)dihydropalmatine.

NMR(300 MHz, CDCl$_3$) δ: 2.55(m, 2H), 3.19(m, 2H), 3.65(d, 1H), 3.80(s, 2H), 3.81(s, 3H), 3.90(s, 3H), 3.92(s, 6H), 4.25(d, 1H), 6.05(d, 1H), 6.64(d, 1H), 6.75(s, 1H), 6.84(d, 2H), 6.85(s, 1H), 7.14(d, 2H)

EXAMPLE 105

Preparation of 13-(3-chlorobenzyl)dihydropalmatine (comp. No. 105)

13-(3-Chlorobenzyl)palmatine iodide(2.0 g) obtained in Example 68, instead of 13-benzylberberine iodide of Example 89, is treated by the process described in Example 89 to obtain 1.63 g of 13-(3-chlorobenzyl)dihydropalmatine.

NMR(300 MHz, CDCl$_3$) δ: 2.80–3.10(m, 4H), 3.58(d, 1H), 3.72(s, 2H), 3.83(s, 3H), 3.88(s, 3H), 3.90(s, 3H), 3.91(s, 3H), 4.21(d, 1H), 6.10(d, 1H), 6.67(d, 1H), 6.69(s, 1H), 7.05–7.15(m, 4H), 7.14(s, 1H)

EXAMPLE 106

Preparation of 13-(2-chlorobenzyl)dihydropalmatine (comp. No. 106)

13-(2-Chlorobenzyl)palmatine iodide(2.0 g) obtained in Example 69, instead of 13-benzylberberine iodide(2.0 g) of Example 89, is treated by the process described in Example 89 to obtain 1.57 g of 13-(2-chlorobenzyl)dihydropalmatine.

NMR(300 MHz, CDCl$_3$) δ: 2.65(m, 2H), 3.17(m, 2H), 3.60(d, 1H), 3.71(s, 2H), 3.79(s, 3H), 3.85(broad s, 9H), 4.15(d, 1H), 6.14(d, 1H), 6.67(d, 1H), 6.70(s, 1H), 6.73(s, 1H), 6.86(d, 1H), 7.02(t, 1H), 7.12(s, 1H), 7.19(s, 1H)

EXAMPLE 107

Preparation of 13-(4-bromobenzyl)dihydropalmatine (comp. No. 107)

13-(4-Bromobenzyl)palmatine iodide(2.0 g) obtained in Example 70, instead of 13-benzylberberine iodide of Example 89, is treated by the process described in Example 89 to obtain 1.63 g of 13-(3-bromobenzyl)dihydropalmatine.

NMR(300 MHz, CDCl$_3$) δ: 2.50(m, 2H), 3.25(m, 2H), 3.64(d, 1H), 3.85(s, 2H), 3.85(s, 3H), 3.90(s, 3H), 3.91(s, 3H), 3.93(s, 3H), 4.27(d, 1H), 6.05(d, 1H), 6.63(d, 1H), 6.70(s, 1H), 6.75(d, 1H), 6.81(s, 1H), 7.17(d, 2H)

EXAMPLE 108

Preparation of 13-(3-bromobenzyl)dihydro palmatine (comp. No. 108)

13-(3-Bromobenzyl)palmatine iodide(2.0 g) obtained in Example 71, instead of 13-benzylberberine iodide of Example 89, is treated by the process described in Example 89 to obtain 1.62 g of 13-(3-bromobenzyl)dihydropalmatine.

NMR(300 MHz, CDCl$_3$) δ: 2.70(m, 2H), 3.20(m, 2H), 3.65(d, 1H), 3.70(s, 2H), 3.75(s, 3H), 3.80(s, 3H), 3.82(s, 3H), 3.83(s, 3H), 4.15(d, 1H), 5.99(d, 1H), 6.65(d, 1H), 6.72(s, 1H), 6.92(d, 1H), 6.95(d, 1H), 7.02–7.02(m, 2H), 7.12(s, 1H)

EXAMPLE 109

Preparation of 13-(4-methylbenzyl) dihydropalmatine (comp. No. 109)

13-(4-Methylbenzyl)palmatine iodide(2.0 g) obtained in Example 72, instead of 13-benzylberberine iodide of Example 89, is treated by the process described in Example 89 to obtain 1.59 g of 13-(4-methylbenzyl) dihydropalmatine.

NMR(300 MHz, CDCl$_3$) δ: 2.25(s, 3H), 2.59(m, 2H), 3.27(m, 2H), 3.66(d, 1H), 3.76(s, 2H), 3.81(s, 3H), 3.85(s, 3H), 3.87(s, 6H), 4.15(d, 1H), 6.21(d, 1H), 6.71(d, 1H), 6.77(s, 1H), 6.85(d, 2H), 6.92(s, 1H), 7.11(d, 2H)

EXAMPLE 110

Preparation of 13-(3-methylbenzyl) dihydropalmatine (comp. No. 110)

13-(3-Methylbenzyl)palmatine iodide (2.0 g)obtained in Example 73, instead of 13-benzyl berberine of Example 89, is treated by the process described in Example 89 to obtain 1.51 g of 13-(3-methylbenzyl)dihydro palmatine.

NMR(300 MHz, CDCl$_3$) δ: 2.20(s, 3H), 2.79(m, 2H), 3.17(m, 2H), 3.59(d, 1H), 3.75(s, 2H), 3.87(s, 3H), 3.90(s, 3H), 3.93(s, 6H), 4.17(d, 1H), 6.13(d, 1H), 6.59(d, 1H), 6.67(s, 1H), 7.04–7.10(m, 4H), 7.12(s, 1H)

EXAMPLE 111

Preparation of 13-(2-methylbenzyl) dihydropalmatine (comp. No. 111)

13-(2-Methylbenzyl)plamatine iodide(2.0 g) obtained in Example 74, instead of 13-benzylberberine iodide of Example 89, is treated by the process described in Example 89 to obtain 1.49 g of 13-(2-methylbenzyl) dihydropalmatine.

NMR(300 MHz, CDCl$_3$) δ: 2.26(s, 3H), 2.79(m, 2H), 3.15(m, 2H), 3.59(d, 1H), 3.75(s, 2H), 3.78(s, 3H), 3.83(s, 3H), 4.16(d, 1H), 6.24(d, 1H), 6.71(d, 1H), 6.73(s, 1H), 6.87(d, 1H), 7.02(t, 1H), 7.06(t, 1H), 7.12(s, 1H), 7.18(d, 1H)

EXAMPLE 112

Preparation of 13-(3,4-dimethylbenzyl)dihydro palmatine (comp. No. 112)

13-(3,4-Dimethylbenzyl)palmatine iodide(2.0 g) obtained in Example 75, instead of 13-benzylberberine iodide of Example 89, is treated by the process described in Example 89 to obtain 1.53 g of 13-(3,4-dimetliylbenzyl)dihydro palmatine.

NMR(300 MHz, CDCl$_3$) δ: 2.17(s, 3H), 2.23(s, 3H), 2.59(m, 2H), 3.10(m, 2H), 3.65(d, 1H), 3.80(s, 2H), 3.85(s, 3H), 3.91(s, 3H), 3.93(s, 6H), 4.15(d, 1H), 6.24(d, 1H), 6.70(d, 1H), 6.73(s, 1H), 6.87(d, 1H), 7.11(d, 1H), 7.16(s, 1H)

EXAMPLE 113

Preparation of 13-(2,4-dimethylbenzyl) dihydropalmatine (comp. No. 113)

13-(2,4-Dimethylbenzyl)palmatine iodide(2.0 g) obtained in Example 76, instead of 13-benzylberberine iodide of Example 89, is treated by the process described in Example 89 to obtain 1.47 g of 13-(2,4-dimethylbenzyl)dihydro palmatine.

NMR(300 MHz, CDCl$_3$) δ: 2.20(s, 3H), 2.22(s, 3H), 2.65(m, 2H), 3.24(m, 2H), 3.65(d, 1H), 3.79(s, 2H), 3.82(s, 3H), 3.87(s, 3H), 3.89(s, 3H), 3.91(s, 3H), 4.21(d, 1H), 6.17(d, 1H), 6.75(d, 1H), 6.82(d, 1H), 7.02(d, 1H), 7.10(d, 1H), 7.14(s, 1H), 7.25(d, 1H)

EXAMPLE 114

Preparation of 13-(4-t-butylbenzyl)dihydropalmatine (comp. No. 114)

13-(4-t-Butylbenzyl)palmatine iodide (2.0 g) obtained in Example 77, instead of 13-benzylberberine iodide of Example 89, is treated by the process described in Example 89 to obtain 1.77 g of 13-(4-t-butylbenzyl) dihydropalmatine.

NMR(300 MHz, CDCl$_3$) δ: 1.22(s, 9H), 2.48(m, 2H), 3.33(m, 2H), 3.65(d, 1H), 3.88(s, 2H), 3.85(s, 3H), 3.90 (broad s, 6H), 3.97(s, 3H), 4.21(d, 1H), 6.15(d, 1H), 6.77(d, 1H), 6.81(s, 1H), 6.87(d, 2H), 7.05(s, 1H), 7.19(d, 2H)

EXAMPLE 115

Preparation of 2,3,9,10-tetrapropoxydihydroprotoberberine (comp. No. 115)

2,3,9,10-Tetrapropoxy protoberberine iodide(2.0 g) obtained in Example 78, instead of 13-benzylberberine iodide of Example 89, is treated by the process described in Example 89 to obtain 1.65 g of 2,3,9,10-tetrapropoxydihydro protoberberine.

NMR(300 MHz, CDCl$_3$) δ: 1.10(m, 12H), 1.90(m, 6H), 2.00(m, 2H), 3.30(t, 2H), 3.90(broad s, 2H), 4.10(m, 6H), 4.47(t, 2H), 5.15(t, 2H), 6.00(s, 1H), 6.31(d, 1H), 6.79(d, 1H), 6.79(s, 1H), 6.85(s, 1H), 7.16(s, 1H)

EXAMPLE 116

Preparation of 8-(n-octyl)dihydroberberine (comp. No. 116)

Mg(0.45 g) was added to 50 ml of anhydrous ether and n-octyl bromide was slowly added thereto dropwise. The reaction was proceeded under reflux for 2 hours, and berberine chloride which had been dried completely was added thereto, and further refluxed for 2 hours. The resulting mixture was concentrated and dried, and then 50 ml of water was added thereto. The solid thus precipitated was filtered off and dried, and then the aqueous phase was extracted twice with 40 ml of dichloromethane and concentrated to obtain 2.12 g of 8-(n-octyl)dihydroberberine NMR(300 MHz, CDCl$_3$) δ: 0.80(t, 3H), 1.10–1.40(m, 12H), 1.82(m, 2H), 2.65(m, 2H), 2.86(m, 2H), 3.76(s, 3H), 3.77(s, 3H), 3.87(s, 3H), 4.07(s, 3H), 5.86(s, 1H), 6.64(d, 1H), 6.76(s, 1H), 6.83(d, 1H), 7.22(s, 1H)

EXAMPLE 117

Preparation of 8-(3-cyclohexylpropyl) dihydroberberine (comp. No. 117)

3-Cyclohexylpropyl bromide, instead of n-octyl bromide of Example 116, was treated by the process described in Example 116 to obtain 2.07 g of 8-(3-cyclohexylpropyl) dihydroberberine.

NMR(300 MHz, CDCl$_3$) δ: 0.80(m, 2H), 0.90–1.20(m, 12H), 1.80(m, 4H), 2.75(m, 2H), 3.24(m, 2H),-3.66(s, 3H), 3.87(s, 3H), 5.92(s, 1H), 6.00(s, 2H), 6.65(d, 1H), 6.67(s, 2H), 6.93td, 1H), 7.27(s, 1H)

EXAMPLE 118

Preparation of 8-(n-octyl)dihydropalmatine (comp. No. 118)

Palmatine chloride, instead of berberine chloride of Example 116, is treated by the process described in Example 116 to obtain 2.15 g of 8-(n-octyl)dihydro palmatine.

NMR(300 MHz, DMSO-d$_6$) δ: 0.80(t, 3H), 1.10–1.40(m, 12H), 1.86(m, 2H), 2.75(m, 2H), 3.24(m, 2H), 3.72(s, 3H), 3.77(s, 3H), 4.58(broad s, 1H), 5.85(s, 2H), 6.05(s, 2H), 6.67(s, 2H), 6.93(s, 1H)

EXAMPLE 119

Preparation of 0.5 % creamy formulation of comp. No. 62

Tefose 63(80 g) produced by GATFEFOSSE in France, 15.32 g of Labrafil M 1944 CS produced by GATTEFOSSE in France and 14.4 g of liquid paraffine were heated to 70° C. and 2 g of the compound No. 62 was added thereto and then suspended with stirring (8,000 rpm) for 10 minutes. The suspension thus obtained was added to water solution at 70° C. wherein 2.0 g of disodium hydrogen phosphate (Na$_2$HPO$_4$) was dissolved in 300 g of purified water, and emulsified with stirring(8,000 rpm) for 20 minutes. The emulsion thus obtained was cooled to 35° C. with stirring and charged in tube by suitable amount.

EXAMPLE 120

Preparation of 0.5% creamy formulation of compound No. 85

Tefose 63(80 g) produced by GATTEFOSSE in France, 15.32 g of Labrafil M 1944 CS and 14.4 g of liquid paraffine were heated to 70° C. and the compound No. 85 was added thereto and then suspended with stirring (8,000 rpm) for 10 minutes. The suspension thus obtained was added to water solution at 70° C. wherein 2.0 g of disodium hydrogen phosphate(Na$_2$HPO$_4$) was dissolved in 300 g of purified water, and emulsified with stirring(8,000 rpm) for 20 minutes. The emulsion thus obtained was cooled to 35° C. and charged in tube by suitable amount.

EXAMPLE 121

Preparation of vaginal suppository of the compound No. 62

The compound No. 62(10 g), 50 g of succinic acid, 100 mg of potassium sulphate, 20 g of silicon dioxide(SiO$_2$) and 180 g of lactose #100(100 Mesh) were mixed in mixer for 5 minutes, and 8,560 g of lactose #100(100 Mesh) and 1,000 g of Ludipress produced by BASF in Germany were added thereto and then mixed for 10 minutes. Magnesium stearate (80 g) was added to the mixture and further mixed for 5 minutes. The resulting mixture was tableted using a punch to prepare 10,000 tablets of which thickness is 6.0 mm and weight is 1,000 mg. (Hardness: 8 KP, Friction loss: 0.2%, Disintegration rate: 120 seconds)

EXAMPLE 122

Preparation of vaginal suppository of the compound No. 85

The compound No. 85(10 g), 50 g of succinic acid, 100 g of potassium sulphate, 20 g of silicon dioxide($SiO_2$) and 180 g of lactose #100(100 Mesh) were mixed in mixer for 5 minutes, and 8,560 g of lactose #100(100 Mesh) and 1,000 g of Ludipress were added thereto and then mixed for 10 minutes. Magnesium stearate(80 g) was added to the mixture and further mixed for 5 minutes. The resulting mixture was tableted using a punch to prepare 10,000 tablets of which thickness is 6.0 mm and weight is 1,000 mg. (Hardness: 8 KP, Friction loss: 0.2%, Disintegration rate: 110 seconds)

EXAMPLE 123

Antifungal efficacy of creamy formulation against local fungal skin infection

Specific pathogen free SKH/1 male mouse(Hairless) of which weight is 30–35 g and age is 5 weeks, was reared with sterilized water and feed for 12 night/day in the condition of 21–23 ° C. and of 50% relative humidity. Five mice were allocated by each group. After skin infection, each mouse was taken in separate cage. The strain of microorganism for infection(*Epidermophyton floccosum*) was cultivated on a flat medium of SDA(Sabouraud Dextrose Agar) for 5–7 days and after confirmation of macrocomidia, 3 ml of RPMI (Rosewell Park Memorial Institute) 1640 media per each flat medium was added thereto and then scraped well using loop to remove hyphae from media. The floating liquid was suspended briefly and then diluted with RPMI 1640 media to adjust the concentration of hyphae to $2\times10^6$ CFU/ml. A Mouse was anesthetized and marked on back (lumbosacral area) in a shape of circle of which diameter is 1.5 cm. Then, the inner part of marked skin was scratched with sand paper. The scratched part was covered with a filter paper to preserve inoculated microorganism for a long time and thereby stimulating the skin continuously. 0.2 ml of fungus solution of which concentration is adjusted as described above, was inoculated between the skin and filter paper. 5 Days after the inoculation, the filter paper was removed and the infection of skin was examined. The test formulations, 0.5% creamy formulations of the compounds Nos. 62 and 85, 1.0% creamy formulation of Terbinafine(Lamisil® cream) and a placebo was applied on the infected areas in a same amount once a day for 5 days. The clinical evaluation on the change of the infected area in 5 days after the inoculation was performed and expressed numerically from 0 to 4. The daily change of the infected area was checked every day. The result of each group was compared with each other.

0: Normal state
1: Mild erythema or small number of skin eruption
2: Well-demarcated erythema with scales or mild skin eruption of infected area
3: Wide area of marked skin eruption, scales, swelling or severe skin eruption with partial swelling and scales
4: The same as those of control, or severe skin eruption in entire lesion The result was calculated as follows;

$$\text{Efficacy}(\%) = 100 - (T \times 100 \div K)$$

T: Average score of clinical evaluation in drug treated area
K: Average score of clinical evaluation in placebo control group Meanwhile, novel compounds having the above chemical formulae Nos. 1 and 2, and the relative activities thereof against *Candida albicans*(KCTC 1940), *Aspergillus niger* (ATCC 9642) and *Saccharomyces cerevisiae* in accordance with the agar dilution method in Sabouraud dextrose agar media, Czapek agar media and Yeast Extract-Peptone-Dextrose agar media, are described respectively in following Tables 1a–1e and 2a–2c. The relative activities of novel compounds are evaluated and expressed as follows: the relative activity is 4 in case that the control drug, i.e., Miconazole exhibits the fungistatic activity in agar media at a certain concentration; the relative activity of the novel compound is 4 in case that the novel compound exhibit the fungicidal activity at the concentration same as that of Miconazole; the relative activities of the novel compound are 3, 2, 1 respectively in case that the novel compound exhibits the fungicidal activity at 2, 4, 8 times higher concentration than that of Miconazole; the relative activities of the novel compound are 5, 6, 7 respectively in case that the novel compound exhibits the fungicidal activity at ½, ¼, ⅛ times lower concentration than that of Miconazole.

TABLE 1A

| | Protoberberine salt derivative (chemical formula I) | | | | | |
|---|---|---|---|---|---|---|
| comp. no. | $R_1, R_2$ | $R_3$ | $R_4$ | A | $R_5$ | relative activity |
| 1 | —O—$CH_2$—O— | —H | —$OCH_3$ | I | —$CH_2$—⌬ | 2 |

TABLE 1A-continued

Protoberberine salt derivative (chemical formula I)

| comp. no. | $R_1, R_2$ | $R_3$ | $R_4$ | A | $R_5$ | relative activity |
|---|---|---|---|---|---|---|
| 2 | —O—CH$_2$—O— | —H | —OCH$_3$ | I | —CH$_2$—C$_6$H$_4$—Cl (para) | 3 |
| 3 | —O—CH$_2$—O— | —H | —OCH$_3$ | I | —CH$_2$—C$_6$H$_4$—Cl (meta) | 3 |
| 4 | —O—CH$_2$—O— | —H | —OCH$_3$ | I | —CH$_2$—C$_6$H$_4$—Cl (ortho) | 3 |
| 5 | —O—CH$_2$—O— | —H | —OCH$_3$ | I | —CH$_2$—C$_6$H$_4$—Br (para) | 3 |
| 6 | —O—CH$_2$—O— | —H | —OCH$_3$ | I | —CH$_2$—C$_6$H$_4$—Br (meta) | 2 |
| 7 | —O—CH$_2$—O— | —H | —OCH$_3$ | Cl | —CH$_2$—C$_6$H$_3$—2,3-Cl$_2$ | 2 |
| 8 | —O—CH$_2$—O— | —H | —OCH$_3$ | Cl | —CH$_2$—C$_6$H$_4$—F (ortho) | 2 |
| 9 | —O—CH$_2$—O— | —H | —OCH$_3$ | Cl | —CH$_2$—C$_6$H$_3$(F)(Cl) | 2 |
| 10 | —O—CH$_2$—O— | —H | —OCH$_3$ | Cl | —CH$_2$—C$_6$H$_3$—2,6-F$_2$ | 2 |
| 11 | —O—CH$_2$—O— | —H | —OCH$_3$ | Cl | —CH$_2$—C$_6$H$_3$—3,4-F$_2$ | 2 |

TABLE 1A-continued

Protoberberine salt derivative (chemical formula I)

| comp. no. | $R_1, R_2$ | $R_3$ | $R_4$ | A | $R_5$ | relative activity |
|---|---|---|---|---|---|---|
| 12 | —O—CH$_2$—O— | —H | —OCH$_3$ | Cl | —CH$_2$—(2-CF$_3$, 5-F phenyl) | 2 |
| 13 | —O—CH$_2$—O— | —H | —OCH$_3$ | Cl | —CH$_2$—(2,3,4,5,6-pentafluorophenyl) | 2 |

TABLE 1B

| comp. no. | $R_1, R_2$ | $R_3$ | $R_4$ | A | $R_5$ | relative activity |
|---|---|---|---|---|---|---|
| 14 | —O—CH$_2$—O— | —H | —OCH$_3$ | Cl | —CH$_2$—(2,3,5,6-tetrafluoro-4-CF$_3$ phenyl) | 2 |
| 15 | —O—CH$_2$—O— | —H | —OCH$_3$ | Cl | —CH$_2$—(4-CH$_3$ phenyl) | 3 |
| 16 | —O—CH$_2$—O— | —H | —OCH$_3$ | Cl | —CH$_2$—(3-CH$_3$ phenyl) | 3 |
| 17 | —O—CH$_2$—O— | —H | —OCH$_3$ | Cl | —CH$_2$—(2-CH$_3$ phenyl) | 3 |
| 18 | —O—CH$_2$—O— | —H | —OCH$_3$ | Cl | —CH$_2$—(3,4-di-CH$_3$ phenyl) | 5 |

TABLE 1B-continued

| comp. no. | $R_1, R_2$ | $R_3$ | $R_4$ | A | $R_5$ | relative activity |
|---|---|---|---|---|---|---|
| 19 | —O—CH$_2$—O— | —H | —OCH$_3$ | Cl | —CH$_2$-(2,4-dimethylphenyl with 5-CH$_3$), 2,4-dimethyl-5-methylbenzyl (2-CH$_3$, 4-CH$_3$ on ring with CH$_3$ para) | 3 |
| 20 | —O—CH$_2$—O— | —H | —OCH$_3$ | Cl | —CH$_2$-(2,5-dimethylphenyl) | 3 |
| 21 | —O—CH$_2$—O— | —H | —OCH$_3$ | Cl | —CH$_2$-(2-nitro-4-methylphenyl) | 2 |
| 22 | —O—CH$_2$—O— | —H | —OCH$_3$ | Cl | —CH$_2$-(3-nitro-4-methylphenyl) | 2 |
| 23 | —O—CH$_2$—O— | —H | —OCH$_3$ | Cl | —CH$_2$-(2-methyl-3-nitrophenyl) | 1 |
| 24 | —O—CH$_2$—O— | —H | —OCH$_3$ | Cl | —CH$_2$-(2-trifluoromethylphenyl) | 1 |
| 25 | —O—CH$_2$—O— | —H | —OCH$_3$ | Cl | —CH$_2$-(3-trifluoromethylphenyl) | 2 |
| 26 | —O—CH$_2$—O— | —H | —OCH$_3$ | Cl | —CH$_2$-(4-trifluoromethylphenyl) | 3 |
| 27 | —O—CH$_2$—O— | —H | —OCH$_3$ | Cl | —CH$_2$-(4-methoxyphenyl) | 3 |

TABLE 1C
| comp. no. | R₁, R₂ | R₃ | R₄ | A | R₅ | relative activity |
|---|---|---|---|---|---|---|
| 28 | —O—CH₂—O— | —H | —OCH₃ | Cl | 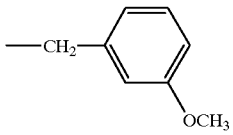 | 3 |
| 29 | —O—CH₂—O— | —H | —OCH₃ | Cl | 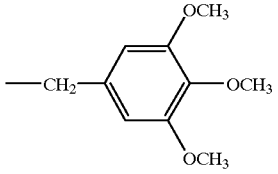 | 4 |
| 30 | —O—CH₂—O— | —H | —OCH₃ | Cl | 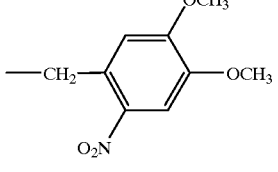 | 3 |
| 31 | —O—CH₂—O— | —H | —OCH₃ | Cl | 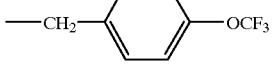 | 4 |
| 32 | —O—CH₂—O— | —H | —OCH₃ | Cl | 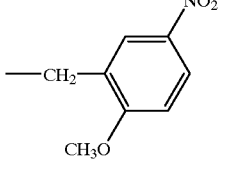 | 3 |
| 33 | —O—CH₂—O— | —H | —OCH₃ | Cl | 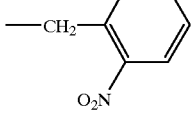 | 3 |
| 34 | —O—CH₂—O— | —H | —OCH₃ | Cl | 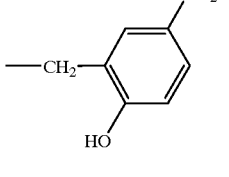 | 3 |
| 35 | —O—CH₂—O— | —H | —OCH₃ | Cl | 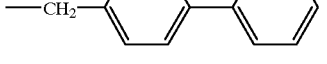 | 6 |
| 36 | —O—CH₂—O— | —H | —OCH₃ | Cl |  | 3 |
| 37 | —O—CH₂—O— | —H | —OCH₃ | Cl | 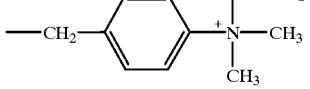 | 5 |

TABLE 1C-continued

| comp. no. | $R_1, R_2$ | $R_3$ | $R_4$ | A | $R_5$ | relative activity |
|---|---|---|---|---|---|---|
| 38 | —O—CH$_2$—O— | —H | —OCH$_3$ | Cl | —CH$_2$—C$_6$H$_4$—N$^+$(CH$_3$)(CH$_3$)(CH$_2$CH$_3$) I$^-$ | 5 |
| 39 | —O—CH$_2$—O— | —H | —OCH$_3$ | Cl | —CH$_2$—C$_6$H$_4$—N$^+$(CH$_3$)(CH$_2$)(CH$_2$—C$_6$H$_5$) Cl$^-$ | 4 |
| 40 | —O—CH$_2$—O— | —H | —OCH$_3$ | Cl | —CH$_2$—C$_6$H$_4$—N$^+$(CH$_3$)(CH$_2$)((CH$_2$)$_5$CH$_3$) I$^-$ | 4 |

TABLE 1D

| comp. no. | $R_1, R_2$ | $R_3$ | $R_4$ | A | $R_5$ | relative activity |
|---|---|---|---|---|---|---|
| 41 | —O—CH$_2$—O— | —H | —OCH$_3$ | Cl | —CH$_2$—(2-F,4-C(CH$_3$)$_3$-C$_6$H$_3$) | 3 |
| 42 | —O—CH$_2$—O— | —H | —OCH$_3$ | Cl | —CH$_2$—(2-NO$_2$,4-C(CH$_3$)$_3$-C$_6$H$_3$) | 3 |
| 43 | —O—CH$_2$—O— | —H | —OCH$_3$ | Cl | —CH$_2$—C$_6$H$_4$—NH—C(=NH)—NH$_2$ | 4 |
| 44 | —O—CH$_2$—O— | —H | —OCH$_3$ | Cl | —CH$_2$—C$_6$H$_4$—NH—C(=O)—CH$_3$ | 2 |
| 45 | —O—CH$_2$—O— | —H | —OCH$_3$ | Cl | —CH$_2$—C$_6$H$_4$—C(=O)OH | 2 |

TABLE 1D-continued

| comp. no. | $R_1, R_2$ | $R_3$ | $R_4$ | A | $R_5$ | relative activity |
|---|---|---|---|---|---|---|
| 46 | —O—CH$_2$—O— | —H | —OCH$_3$ | Cl | —CH$_2$—C$_6$H$_4$—C(CH$_3$)$_2$OH | 2 |
| 47 | —O—CH$_2$—O— | —H | —OCH$_3$ | Cl | —CH$_2$—C$_6$H$_4$—OCH(CH$_3$)$_2$ | 2 |
| 48 | —O—CH$_2$—O— | —H | —OCH$_3$ | Cl | —CH$_2$—C$_6$H$_4$—CH(CH$_3$)CH$_2$CH$_3$ | 3 |
| 49 | —O—CH$_2$—O— | —H | —OCH$_3$ | Cl | —CH$_2$—C$_6$H$_4$—C(CH$_3$)$_2$CH$_2$CH$_3$ | 4 |
| 50 | —O—CH$_2$—O— | —H | —OCH$_3$ | Cl | —CH$_2$—C$_6$H$_4$-pyrrolidinyl | 4 |
| 51 | —O—CH$_2$—O— | —H | —OCH$_3$ | Cl | —CH$_2$—C$_6$H$_4$—COOH (meta) | 3 |
| 52 | —O—CH$_2$—O— | —H | —OCH$_3$ | Cl | —CH$_2$—C$_6$H$_4$—O—CH(CH$_2$CH$_3$)$_2$ | 3 |
| 53 | —O—CH$_2$—O— | —H | —OCH$_3$ | Cl | —CH$_2$—C$_6$H$_4$—C(O)OCH$_2$CH$_3$ | 3 |

TABLE 1E

| comp. no. | R₁, R₂ | R₃ | R₄ | A | R₅ | relative activity |
|---|---|---|---|---|---|---|
| 54 | —O—CH₂—O— | —H | —OCH₃ | Cl | —CH₂—C₆H₄—SCH₃ (para) | 2 |
| 55 | —O—CH₂—O— | —H | —OCH₃ | Cl | —CH₂—C₆H₄—SCH₂CH₃ (para) | 2 |
| 56 | —O—CH₂—O— | —H | —OCH₃ | Cl | —CH₂—C₆H₄—I (para) | 2 |
| 57 | —O—CH₂—O— | —H | —OCH₃ | Cl | —CH₂—C₆H₄—CH(CH₃)CH₂OH (para) | 3 |
| 58 | —O—CH₂—O— | —H | —OCH₃ | Cl | —CH₂—C₆H₄—O—C₆H₅ (meta) | 5 |
| 59 | —O—CH₂—O— | —H | —OCH₃ | Cl | —CH₂—C₆H₄—O—CH₂C₆H₅ (para) | 4 |
| 60 | —O—CH₂—O— | —H | —OCH₃ | Cl | —CH₂—C₆H₄—CH=CH₂ (para) | 4 |
| 61 | —O—CH₂—O— | —H | —OCH₃ | Cl | —CH₂—C₆H₄—CO₂CH₃ (para) | 3 |
| 62 | —O—CH₂—O— | —H | —OCH₃ | Cl | —CH₂—C₆H₄—C(CH₃)₃ (para) | 7 |
| 63 | —O—CH₂—O— | —H | —OCH₃ | Cl | —CH₂—C₆H₄—CH(CH₃)₂ (para) | 7 |
| 64 | —O—CH₂—O— | —H | —OCH₃ | Cl | —CH₂—C₆H₄—C(CH₃)₃ (para) | 6 |
| 65 | —O—CH₂—O— | —H | —OCH₃ | Cl | —CH₂-(2-pyridyl) | 3 |

TABLE 1E-continued

| comp. no. | $R_1, R_2$ | $R_3$ | $R_4$ | A | $R_5$ | relative activity |
|---|---|---|---|---|---|---|
| 66 | —OCH$_3$ | —H | —OCH$_3$ | I | 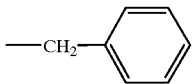 —CH$_2$—C$_6$H$_5$ | 3 |
| 67 | —OCH$_3$ | —H | —OCH$_3$ | I | 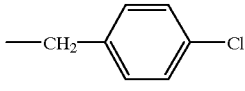 —CH$_2$—(4-Cl-C$_6$H$_4$) | 3 |
| 68 | —OCH$_3$ | —H | —OCH$_3$ | I | 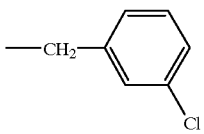 —CH$_2$—(3-Cl-C$_6$H$_4$) | 3 |
| 69 | —OCH$_3$ | —H | —OCH$_3$ | I | 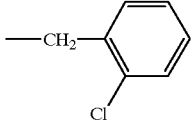 —CH$_2$—(2-Cl-C$_6$H$_4$) | 3 |

TABLE 1F

| comp. no. | $R_1, R_2$ | $R_3$ | $R_4$ | A | $R_5$ | relative activity |
|---|---|---|---|---|---|---|
| 70 | —OCH$_3$ | —H | —OCH$_3$ | I | 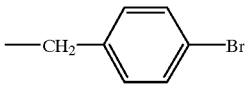 —CH$_2$—(4-Br-C$_6$H$_4$) | 3 |
| 71 | —OCH$_3$ | —H | —OCH$_3$ | I | 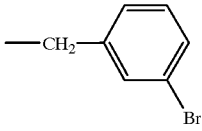 —CH$_2$—(3-Br-C$_6$H$_4$) | 2 |
| 72 | —OCH$_3$ | —H | —OCH$_3$ | I | 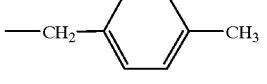 —CH$_2$—(4-CH$_3$-C$_6$H$_4$) | 3 |
| 73 | —OCH$_3$ | —H | —OCH$_3$ | I | 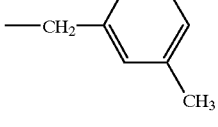 —CH$_2$—(3-CH$_3$-C$_6$H$_4$) | 3 |
| 74 | —OCH$_3$ | —H | —OCH$_3$ | I | 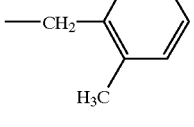 —CH$_2$—(2-CH$_3$-C$_6$H$_4$) | 3 |

TABLE 1F-continued
| comp. no. | $R_1, R_2$ | $R_3$ | $R_4$ | A | $R_5$ | relative activity |
|---|---|---|---|---|---|---|
| 75 | —OCH$_3$ | —H | —OCH$_3$ | I | 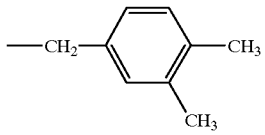 | 4 |
| 76 | —OCH$_3$ | —H | —OCH$_3$ | I | 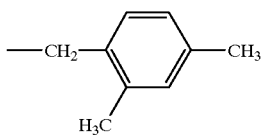 | 4 |
| 77 | —OCH$_3$ | —H | —OCH$_3$ | I | 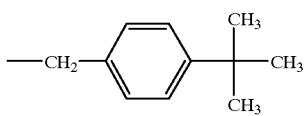 | 6 |
| 78 | —OCH$_3$ | —H | —OCH$_3$ | I | 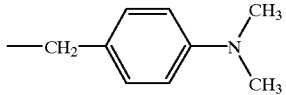 | 3 |
| 79 | —OCH$_3$ | —H | —OCH$_3$ | I | 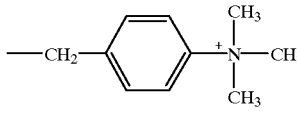 | 4 |
| 80 | —OCH$_3$ | —H | —OCH$_3$ | I | 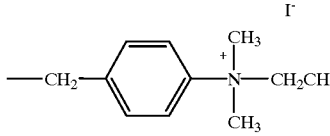 | 4 |
| 81 | —OCH$_3$ | —H | —OCH$_3$ | I | 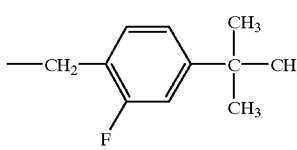 | 3 |
| 82 | —OCH$_3$ | —H | —OCH$_3$ | I | 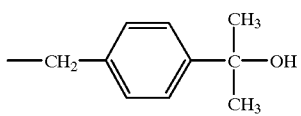 | 3 |

TABLE 1G

| comp. no. | $R_1, R_2$ | $R_3$ | $R_4$ | A | $R_5$ | relative activity |
|---|---|---|---|---|---|---|
| 83 | —OCH₃ | —H | —OCH₃ | I | —CH₂—C₆H₄—CH(CH₃)CH₂CH₃ (with CH₃) | 2 |
| 84 | —OCH₃ | —H | —OCH₃ | I | —CH₂—C₆H₄—SCH₃ | 3 |
| 85 | —OPr | —H | —OPr | I | —H | 6 |
| 86 | —O—CH₂—O— | —H | —OCH₃ | HSO₄⁻ | —CH₂—C₆H₄—C(CH₃)₃ | 4 |
| 87 | —O—CH₂—O— | —H | —OCH₃ | CH₃CO₂⁻ | —CH₂—C₆H₄—C(CH₃)₃ | 4 |
| 88 | —OCH₃ | —H | —OCH₃ | NO₃⁻ | —CH₂—C₆H₄—C(CH₃)₃ | 3 |

TABLE 2A

| comp. no. | $R_1, R_2$ | $R_3$ | $R_4$ | $R_5$ | relative activity |
|---|---|---|---|---|---|
| 89 | —O—CH₂—O— | —H | —OCH₃ | —CH₂—C₆H₅ | 2 |
| 90 | —O—CH₂—O— | —H | —OCH₃ | —CH₂—C₆H₄—Cl (para) | 3 |
| 91 | —O—CH₂—O— | —H | —OCH₃ | —CH₂—C₆H₄—Cl (meta) | 3 |
| 92 | —O—CH₂—O— | —H | —OCH₃ | —CH₂—C₆H₄—Cl (ortho) | 3 |

TABLE 2A-continued

| comp. no. | $R_1, R_2$ | $R_3$ | $R_4$ | $R_5$ | relative activity |
|---|---|---|---|---|---|
| 93 | —O—CH$_2$—O— | —H | —OCH$_3$ | —CH$_2$—C$_6$H$_4$—Br (para) | 3 |
| 94 | —O—CH$_2$—O— | —H | —OCH$_3$ | —CH$_2$—C$_6$H$_4$—Br (meta) | 2 |
| 95 | —O—CH$_2$—O— | —H | —OCH$_3$ | —CH$_2$—C$_6$H$_4$—CH$_3$ (para) | 3 |
| 96 | —O—CH$_2$—O— | —H | —OCH$_3$ | —CH$_2$—C$_6$H$_4$—CH$_3$ (meta) | 3 |
| 97 | —O—CH$_2$—O— | —H | —OCH$_3$ | —CH$_2$—C$_6$H$_4$—CH$_3$ (ortho) | 3 |
| 98 | —O—CH$_2$—O— | —H | —OCH$_3$ | —CH$_2$—C$_6$H$_3$(CH$_3$)$_2$ (3,4-di) | 3 |
| 99 | —O—CH$_2$—O— | —H | —OCH$_3$ | —CH$_2$—C$_6$H$_3$(CH$_3$)$_2$ (2,4-di) | 3 |
| 100 | —O—CH$_2$—O— | —H | —OCH$_3$ | —CH$_2$—C$_6$H$_4$—C(CH$_3$)$_3$ (para) | 5 |
| 101 | —O—CH$_2$—O— | —H | —OCH$_3$ | —CH$_2$-(4-pyridyl) | 2 |
| 102 | —O—CH$_2$—O— | —H | —OCH$_3$ | —CH$_2$—C$_6$H$_3$(NO$_2$)(OH) | 2 |

TABLE 2B
| comp. no. | $R_1$ | $R_2$ | $R_3$ | $R_4$ | $R_5$ | relative activity |
|---|---|---|---|---|---|---|
| 103 | —OCH₃ | —OCH₃ | —H | —OCH₃ | 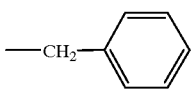 | 3 |
| 104 | —OCH₃ | —OCH₃ | —H | —OCH₃ | 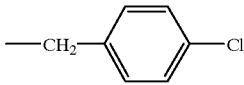 | 3 |
| 105 | —OCH₃ | —OCH₃ | —H | —OCH₃ | 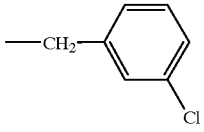 | 2 |
| 106 | —OCH₃ | —OCH₃ | —H | —OCH₃ | 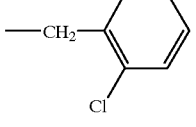 | 2 |
| 107 | —OCH₃ | —OCH₃ | —H | —OCH₃ | 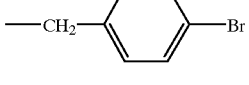 | 2 |
| 108 | —OCH₃ | —OCH₃ | —H | —OCH₃ | 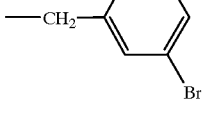 | 2 |
| 109 | —OCH₃ | —OCH₃ | —H | —OCH₃ | 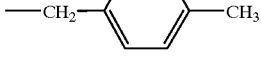 | 3 |
| 110 | —OCH₃ | —OCH₃ | —H | —OCH₃ | 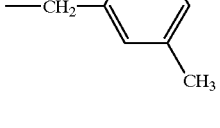 | 2 |
| 111 | —OCH₃ | —OCH₃ | —H | —OCH₃ | 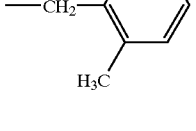 | 2 |
| 112 | —OCH₃ | —OCH₃ | —H | —OCH₃ | 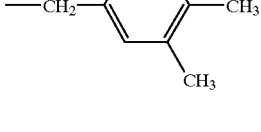 | 3 |
| 113 | —OCH₃ | —OCH₃ | —H | —OCH₃ | 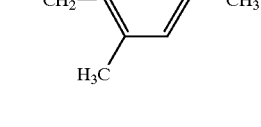 | 3 |

TABLE 2B-continued

| comp. no. | $R_1$ | $R_2$ | $R_3$ | $R_4$ | $R_5$ | relative activity |
|---|---|---|---|---|---|---|
| 114 | —$OCH_3$ | —$OCH_3$ | —H | —$OCH_3$ | —$CH_2$—C$_6$H$_4$—C($CH_3$)$_3$ | 3 |
| 115 | —OPr | —OPr | —H | —OPr | —H | 5 |
| 116 | —O—$CH_2$—O— | | —$C_8H_{17}$ | —$OCH_3$ | —H | 3 |
| 117 | —O—$CH_2$—O— | | —$CH_2$—Cy—Hex | —$OCH_3$ | —H | 3 |
| 118 | —$OCH_3$ | —$OCH_3$ | —$C_8H_{17}$ | —$OCH_3$ | —H | 3 |

The compounds of the above Table 1. are the first compounds which inhibit concurrently *Chitin synthetase* which take part in biosynthesis of chitin, i.e., the constituent component of the cell wall of fungus and sterol 24-methyl transferase, one of the major enzymes for the distal biosynthetic pathway of Ergosterol which is the constituent component of the cell membrane. The MIC. data of the compounds Nos. 18, 29, 31, 35, 58, 60, 63, 64, 77 and 85, and the drugs for control, azole compound, i.e., Miconazole, Itraconazole and Amphotericin B against Candida and Epidermophyton are described in the following Table 3a and 3b.

TABLE 3A

MIC. data of the compounds

| fungus | MIC ($\mu$g/ml) | | | | | | |
|---|---|---|---|---|---|---|---|
| | comp. no. 18 | comp. no. 29 | comp. no. 31 | comp. no. 35 | comp. no. 58 | comp. no. 60 | comp. no. 62 |
| *C. albicans* ATCC 10231 | | | | 6.25 | | | 6.25 |
| *C. albicans* ATCC 28838 | 3.125 | 3.125 | 0.78 | 1.56 | 3.125 | 3.125 | 0.78 |
| *C. albicans* ATCC 11651 | 3.125 | 1.56 | 1.56 | 0.78 | 12.5 | 6.25 | 0.78 |
| *C. albicans* KCTC 1940 | 6.25 | 1.56 | 1.56 | 0.78 | 12.5 | 6.25 | 0.78 |
| *C. albicans* U. K. | | | | 12.5 | | | 6.25 |
| *C. albicans* OY 109 | 6.25 | 6.25 | 1.56 | 1.56 | 12.5 | 12.5 | 0.78 |
| *C. albicans* OY 003 | 6.25 | 6.25 | 1.56 | 0.78 | 6.25 | 6.25 | 0.78 |
| *C. albicans* IFO 1385 | 12.5 | 25 | 3.125 | 6.25 | 25 | 25 | 6.25 |
| *C. parapsilosis* | | | | >100 | | | >100 |
| *C. glabrata* | | | | >100 | | | >100 |
| *C. glulliermendi* | | | | 12.5 | | | 12.5 |
| *C. krusei* | | | | 3.125 | | | 3.125 |
| *E. floccosum* | | | | 12.5 | | | 12.5 |

TABLE 3B

| fungus | MIC ($\mu$g/ml) | | | | | | |
|---|---|---|---|---|---|---|---|
| | comp. no. 63 | comp. no. 64 | comp. no. 77 | comp. no. 85 | Miconazole | Itraconazole | Amphotericin B |
| *C. albicans* ATCC 10231 | 6.25 | | | 6.25 | 6.25 | | 1.56 |
| *C. albicans* ATCC 28838 | 0.78 | 3.125 | 0.78 | 0.78 | 0.78 | >100 | 3.125 |
| *C. albicans* ATCC 11651 | 0.78 | 3.125 | 0.78 | 0.4 | 3.125 | >100 | 1.56 |
| *C. albicans* KCTC 1940 | 1.56 | 12.5 | 1.56 | 0.4 | 1.56 | >100 | 0.78 |
| *C. albicans* U. K. | 6.25 | | | 50 | >100 | | 3.125 |
| *C. albicans* OY 019 | 1.56 | 0.4 | 1.56 | 0.4 | 1.56 | >100 | 0.4 |
| *C. albicans* OY 003 | 6.25 | 6.25 | 0.78 | 0.4 | 1.56 | >100 | 0.78 |
| *C. albicans* IFO 1385 | 6.25 | 25 | 3.125 | 6.25 | 3.125 | >100 | 1.56 |

TABLE 3B-continued

| | MIC (μg/ml) | | | | | | |
|---|---|---|---|---|---|---|---|
| fungus | comp. no. 63 | comp. no. 64 | comp. no. 77 | comp. no. 85 | Mico-nazole | Itraco-nazole | Amphot ericin B |
| C. parapsilosis | >100 | | | 12.5 | 3.125 | | 3.125 |
| C. glabrata | >100 | | | >100 | >100 | | 1.56 |
| C. glulliermendi | 12.5 | | | >100 | | 3.125 | 1.56 |
| C. krusei | 3.125 | | | 1.56 | 3.125 | | 0.78 |
| E. floccosum | 12.5 | >100 | | >100 | 6.25 | 50 | 12.5 |

Moreover, the antifungal efficacies of the 0.5% creamy formulation of the compounds Nos. 29, 35, 60, 62, 63 and 85, and 1% creamy formulation of Terbinafine (Lamisil cream), which are measured by applying the above formulations on the skin infected with *Epidermophyton floccosum* of mouse which is the standard animal for the test of local fungal skin infection, i.e., Specific Pathogen Free SKH/1, are described in the following Table 4.

TABLE 4

Antifungal efficacy against local fungal skin infection.

| | Efficacy (%) | | | | | | | |
|---|---|---|---|---|---|---|---|---|
| | 0 day later | 1 day later | 2 day later | 3 day later | 4 day later | 5 day later | 6 day later | 7 day later |
| comp no. 62 (0.5%) | 0 | 40.0 | 55.4 | 69.4 | 72.6 | 76.3 | 79.2 | 85.4 |
| comp no. 63 (0.5%) | 0 | 42.5 | 52.5 | 59.8 | 64.6 | 73.6 | 75.6 | 80.2 |
| comp no. 35 (0.5%) | 0 | 36.0 | 57.9 | 68.4 | 72.2 | 74.0 | 75.4 | 76.8 |
| comp no. 85 (0.5%) | 0 | 34.5 | 38.8 | 42.5 | 54.6 | 63.2 | 68.0 | 70.5 |
| comp no. 29 (0.5%) | 0 | 30.0 | 33.4 | 34.6 | 48.0 | 56.4 | 63.0 | 65.8 |
| comp no. 60 (0.5%) | 0 | 20.0 | 32.0 | 36.0 | 48.6 | 51.5 | 58.6 | 60.5 |
| Terbinabin (1.0%) | 0 | 40.0 | 57.9 | 68.4 | 70.2 | 71.4 | 73.4 | 75.7 |
| Placebo | 0 | 0 | 0 | 0 | 0 | 0 | 0 | 0 |

The above 0.5% creamy formulation of the compound No. 62 was applied on infected area of 10 male patients with fungal infection of foot, in a proper amount once a day for five days. 8 Patients exhibit remedial effect more than 98%.

Meanwhile, the toxicity test of the compound of the present invention was performed using mouse. The compound was suspended in propylene glycol. The resulting suspension was medicated respectively on 5 female rats and 5 male rats(SD) of which age are 5 weeks, via oral after 12 hour starvation. The general symtoms, weight change and lethal case of the above rats were investigated. In cases of tests of the compound Nos. 25, 62, 63 and 85 (delivery of 2,000 mg/kg), the general sympton and weight change were normal and the lethal case was not observed. Moreover, the bacterial reverse mutation test (Ames test) using salmonella typhimurium, the chromosome aberration test using cultured lung cells derived from chinese hamster and the micronucleous test using male ICR mice on the compounds Nos. 25, 62, 63 and 85 exhibit negative results without exception. The toxicity data on the compound Nos. 25, 62, 63 and 85 are described in the following Table 5. In light forgoings, the compounds of the present invention are safe in toxicity and have the excellent lethal effect and growth-inhibition effect against fungus.

TABLE 5

The toxicity data on compounds Nos. 25, 62, 63 and 85

| | acute toxicity (mg/kg) | | | | genetic toxicity | | |
|---|---|---|---|---|---|---|---|
| comp. no. | animal | delivery route | sex | $LD_{50}$ | AMES test | chromosome abnormality test | nucleus test |
| comp. no. 25 | rats | oral | male | >3,000 | negative | negative | negative |
| | | | female | >2,500 | | | |
| comp. no. 62 | rats | oral | male | >3,700 | negative | negative | negative |
| | | | female | >2,700 | | | |
| comp. no. 63 | rats | oral | male | >2,500 | negative | negative | negative |
| | | | female | >2,000 | | | |
| comp. no. 85 | rats | oral | male | >5,000 | negative | negative | negative |
| | | | female | >5,000 | | | |

The more pertinent important features of the present invention have been outlined above in order that the present contribution to the art can be fully appreciated. Those skilled in the art can appreciate that the conception and the specific embodiment disclosed herein may be readily utilized as a basis for modifying or designing other structures for carrying out the same purposes of the present invention. Further, those skilled in the art can realize that such equivalent constructions do not depart from the spirit and scope of the invention as set forth in the claims.

What is claimed is:

1. An antifungal formulation containing an effective amount of protoberberine salts derivatives of the following chemical formula (I), and pharmaceutically allowable excipient

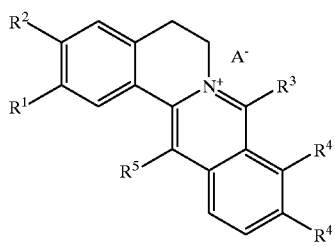

(I)

wherein $R^1$ and $R^2$ may be the same or different, and is selected from the group consisting of $C_1$–$C_5$ alkoxy and methylenedioxy (—O—CH$_2$—O), $R^3$ is selected from the group consisting of hydroxy, cyclohexylmethyl, hydrogen and $C_1$–$C_{10}$ alkyl, A– is selected from the group consisting of inorganic acid ion, organic acid ion and halide, $R^4$ represents $C_1$–$C_5$ alkoxy. and $R^5$ is selected from the group consisting of pyridylmethyl and a group having the following chemical formula (XI)

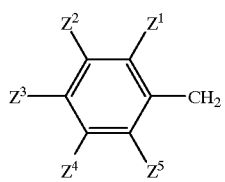

(XI)

wherein $Z^1$, $Z^2$, $Z^3$, $Z^4$ and $Z^5$ may be the same or different, and independently of one another represent hydrogen, Cl, Br, I, $C_1$–$C_5$ alkyl, trifluoromethyl, phenyl, nitro, $C_1$–$C_4$ alkoxy, $C_1$–$C_4$ alkylamino, acetylamino, $C_1$–$C_8$ trialkyl ammonium, guanidinyl, methylthio, ethylthio trifluoromethoxy, hydroxy, phenoxy, vinyl, carboxyl or $C_1$–$C_2$ alkoxycarbonyl group.

2. The antifungal formulation according to claim 1, wherein A– is a group selected from the group consisting of nitrate, sulfate, acetate, tartrate, maleate, succinate, citrate, fumarate, aspartate, salicylate, glycerate, ascorbate, fluoride, chloride, iodide and bromide.

3. The antifungal formulation according to claim 1, wherein $R^1$-$R^2$ is methylenedioxy(—O—CH$_2$—O—), $R^3$ is hydrogen, $R^4$ is methoxy, $R^5$ is 3,4-dimethyl benzyl and A– is chloride.

4. The antifungal formulation according to claim 1, wherein $R^1$-$R^2$ is methylenedioxy(—O—CH$_2$—O—), $R^3$ is hydrogen, $R^4$ is methoxy, $R^5$ is 4-(tert-butyl) benzyl and A– is chloride.

5. The antifungal formulation according to claim 1, wherein $R^1$-$R^2$ is methylenedioxy (—O—CH$_2$—O—), $R^3$ is hydrogen, $R^4$ is methoxy, $R^5$ is 4-phenyl benzyl and A– is chloride.

6. The antifungal formulation according to claim 1, wherein $R^1$-$R^2$ is methylenedioxy(—O—CH$_2$—O—), $R^3$ is hydrogen, $R^4$ is methoxy, $R^5$ is 4-isopropyl benzyl and A– is chloride.

7. The antifungal formulation according to claim 1, wherein $R^1$ is methoxy, $R^2$ is methoxy, $R^3$ is hydrogen, $R^4$ is methoxy, $R^5$ is 4-(tert-butyl) benzyl and A– is iodide.

8. The antifungal formulation according to claim 1, wherein $R^1$ is propoxy, $R^2$ is propoxy, $R^3$ is hydrogen, $R^4$ is propoxy, $R^5$ is hydrogen and A– is iodide.

9. The antifungal formulation according to claim 1 wherein $R^5$ is selected from the group consisting of benzyl, 4-chlorobenzyl, 3-chlorobenzyl, 2-chlorobenzyl, 4-bromobenzyl, 3-bromobenzyl, 2-bromobenzyl, 2,3-dichlorobenzyl, 2-fluorobenzyl, 2-chloro-6-fluorobenzyl, 2,6-difluorobenzyl, 3,4-difluorobenzyl, 4-fluoro-2-trifluoromethylbenzyl, 2,3,4,5,6-pentafluorobenzyl, 2,3,5,6-tetrafluoro-4-trifluoromethylbenzyl, 4-methylbenzyl, 3-methylbenzyl, 2-methylbenzyl, 3,4-dimethylbenzyl, 2,4-dimethylbenzyl, 2,5-dimethylbenzyl, 5-methyl-2-nitrobenzyl, 4-methyl-3-nitrobenzyl, 2-methyl-3-nitrobenzyl, 2-trifluoromethylbenzyl, 3-trifluoromethylbenzyl, 4-trifluoromethylbenzyl, 4-methoxybenzyl, 3-methoxybenzyl, 3,4,5-trimethoxybenzyl, 4,5-dimethoxy-2-nitrobenzyl, 4-trifluoromethoxybenzyl, 2-methoxy-5-nitrobenzyl, 2-nitrobenzyl, 2-hydroxy-5-nitrobenzyl, 4-phenylbenzyl, 4-(N,N-dimethylamino)benzyl, N'-methylammonium iodide of 4-(N,N-dimethylamino)benzyl, N'-ethylammonium iodide of 4-(N,N-dimethylamino)benzyl, N'-benzylammonium chloride of 4-(N,N-dimethylamino) benzyl, N'-hexylammonium iodide of 4-(N,N-dimethylamino)benzyl, 2-fluoro-4-t-butylbenzyl, 2-nitro-4-t-butylbenzyl, 4-guanidinylbenzyl, 4-acetylaminobenzyl, 4-carboxybenzyl, 4-(2-hydroxy-2-propyl)benzyl, 4-isopropoxybenzyl, 4-(2-butyl) benzyl, 4-((2-methyl)-2-butyl)benzyl, 4-pyrrolidinylbenzyl, 3-carboxybenzyl, 4-(3-pentoxy)benzyl, 4-(ethoxycarbonyl)benzyl, 4-methylthiobenzyl, 4-ethylthiobenzyl, 4-iodobenzyl, 4-(1-hydroxy-2-propyl)benzyl, 3-phenoxybenzyl, 4-benzyloxybenzyl, 4-vinylbenzyl, 4-methoxycarbonylbenzyl, 4-t-butylbenzyl, 4-isopropylbenzyl, and 2-picolyl.

10. A method for treating diseases induced by fungi which comprises administering into a patient in need thereof a pharmaceutically eppective amount of 7,8-dihydroprotoberberine salts derivatives of the following chemical formula(II), and pharmaceutically allowable excipient

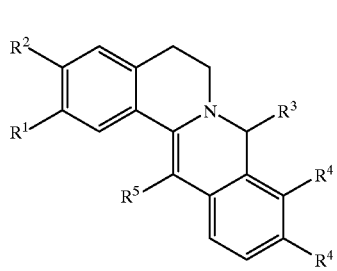

(II)

wherein $R^1$ and $R^2$ may be the same or different, and is selected from the group consisting of $C_1$–$C_5$ alkoxy and methylenedioxy (—O—CH$_2$—) R$^3$ is selected from the group consisting of hydroxy, caclohexylmethyl, hydrogen and C$_1$–C$_{10}$ alkyl, R$^4$ represents C$_1$–C$_5$ alkoxy, and R$^5$ is selected from the group consisting of hydrogen, pyridylmethyl and a group having the following chemical formula (XI)

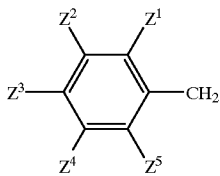

(XI)

wherein Z$^1$, Z$^2$, Z$^3$, Z$^4$ and Z$^5$ may be the same or different, and independently of one another represent hydrogen, Cl, Br, I, C$_1$–C$_5$ alkyl, trifluoromethyl, phenyl, nitro, C$_1$–C$_4$ alkoxy, C$_1$–C$_4$ alkylamino, acetylamino, C$_1$–C$_8$ trialkyl ammonium, guanidinyl, methylthio, ethylthio, trifluoromethoxy, hydroxy, phenoxy, vinyl, carboxyl, or C$_1$–C$_2$ alkoxycarbonyl group.

11. The method according to claim 10 wherein R$^1$-R$^2$ is methylenedioxy(—O—CH$_2$—O—), R$^3$ is octyl(—C$_8$H$_{17}$), R$^4$ is methoxy and R$^5$ is hydrogen.

12. The method according to claim 10 wherein R$^1$ is propoxy, R$^2$ is propoxy, R$^3$ is hydrogen, R$^4$ is propoxy, R$^5$ is hydrogen.

13. The method for treating diseases induced by fungi according to claim 10, wherein R$^5$ is selected from the group consisting of benzyl, 4-chlorobenzyl, 3-chlorobenzyl, 2-chlorobenzyl, 4-bromobenzyl, 3-bromobenzyl, 2-bromobenzyl, 2,3-dichlorobenzyl, 2-fluorobenzyl, 2-chloro-6-fluorobenzyl, 2,6-difluorobenzyl, 3,4-difluorobenzyl, 4-fluoro-2-trifluoromethylbenzyl, 2,3,4,5,6-pentafluorobenzyl, 2,3,5,6-tetrafluoro-4-trifluoromethylbenzyl, 4-methylbenzyl, 3-methylbenzyl, 2-methylbenzyl, 3,4-dimethylbenzyl, 2,4-dimethylbenzyl, 2,5-dimethylbenzyl, 5-methyl-2-nitrobenzyl, 4-methyl-3-nitrobenzyl, 2-methyl-3-nitrobenzyl, 2-trifluoromethylbenzyl, 3-trifluoromethylbenzyl, 4-trifluoromethylbenzyl, 4-methoxybenzyl, 3-methoxybenzyl, 3,4,5-trimethoxybenzyl, 4,5-dimethoxy-2-nitrobenzyl, 4-trifluoromethoxybenzyl, 2-methoxy-5-nitrobenzyl, 2-nitrobenzyl, 2-hydroxy-5-nitrobenzyl, 4-phenylbenzyl, 4-(N,N-dimethylamino)benzyl, N'-methylammonium iodide of 4-(N,N-dimethylamino)benzyl, N'-ethylammonium iodide of 4-(N,N-dimethylamino)benzyl, N'-benzylammonium chloride of 4-(N,N-dimethylamino)benzyl, N'-hexylammonium iodide of 4-(N,N-dimethylamino)benzyl, 2-fluoro-4-t-butylbenzyl, 2-nitro-4-t-butylbenzyl, 4-guanidinylbenzyl, 4-acetylaminobenzyl, 4-carboxybenzyl, 4-(2-hydroxy-2-propyl)benzyl, 4-isopropoxybenzyl, 4-(2-butyl)benzyl, 4-((2-methyl)-2-butyl)benzyl, 4-pyrrolidinylbenzyl, 3-carboxybenzyl, 4-(3-pentoxy)benzyl, 4-(ethoxycarbonyl)benzyl, 4-methylthiobenzyl, 4-ethylthiobenzyl, 4-iodobenzyl, 4-(1-hydroxy-2-propyl)benzyl, 3-phenoxybenzyl, 4-benzyloxybenzyl, 4-vinylbenzyl, 4-methoxycarbonylbenzyl, 4-t-butylbenzyl, 4-isopropylbenzyl, and 2-picolyl.

* * * * *